US008273018B1

(12) United States Patent
Fackler et al.

(10) Patent No.: US 8,273,018 B1
(45) Date of Patent: Sep. 25, 2012

(54) COMPUTERIZED METHOD FOR ESTABLISHING A COMMUNICATION BETWEEN A BEDSIDE CARE LOCATION AND A REMOTE CARE LOCATION

(75) Inventors: James C. Fackler, Baltimore, MD (US); Deepa R. Desai-Deendar, Shawnee, KS (US); Amy Francois, Lee's Summit, MO (US); Stephanie L. Rogers, Kansas City, MO (US)

(73) Assignee: Cerner Innovation, Inc., Lenexa, KS (US)

( * ) Notice: Subject to any disclaimer, the term of this patent is extended or adjusted under 35 U.S.C. 154(b) by 138 days.

(21) Appl. No.: 11/023,906

(22) Filed: Dec. 28, 2004

(51) Int. Cl.
*A61B 5/00* (2006.01)
*G08B 5/00* (2006.01)
*G06Q 50/00* (2012.01)

(52) U.S. Cl. .................. 600/300; 600/301; 340/539.12; 705/2; 705/3; 128/903; 128/904

(58) Field of Classification Search .......... 600/300–301; 128/903–905, 920
See application file for complete search history.

(56) References Cited

U.S. PATENT DOCUMENTS

| | | | |
|---|---|---|---|
| 5,348,008 A | 9/1994 | Bornn et al. | |
| 5,441,047 A | 8/1995 | David | |
| 5,447,164 A | 9/1995 | Shaya et al. | |
| 5,520,191 A | 5/1996 | Karlsson et al. | |
| 5,544,649 A * | 8/1996 | David et al. ............ | 600/301 |
| 5,544,661 A | 8/1996 | Davis et al. | |
| 5,576,952 A | 11/1996 | Stutman et al. | |
| 5,678,562 A | 10/1997 | Sellers | |
| 5,687,717 A | 11/1997 | Halpern | |
| 5,701,894 A | 12/1997 | Cherry et al. | |

(Continued)

FOREIGN PATENT DOCUMENTS
WO    WO9829790    7/1998

OTHER PUBLICATIONS

Rendina, et al., "The Effect of Telemedicine on Neonatal Intensive Care Unit Length of Stay in Very Low Birthweight Infants," Department of Health Policy and Administration, School of Public Health, University of North Carolina Hospitals Information Services Division, University of North Carolina, Chapel Hill, NC.

(Continued)

*Primary Examiner* — Henry M Johnson, III
*Assistant Examiner* — Bobby Soriano
(74) *Attorney, Agent, or Firm* — Shook, Hardy & Bacon L.L.P.

(57) ABSTRACT

Methods for use in, e.g., a patient care computing environment, for establishing a communication between a bedside care location and a remote care location are provided. In one embodiment, the method may include providing a multi-patient view having a plurality of selectable patient indicators and receiving an indication that one of the plurality of selectable patient indicators has been selected by a user. In another embodiment, the method may include displaying a view of an electronic record associated with a patient, e.g., an electronic medical record, the view having a selectable audio/video launch indicator, and receiving an indication that the selectable audio/video indicator has been selected by a user. The user's selection of one of the plurality of selectable patient indicators or the selectable audio/video indicator may be indicative of a request for initiation of a communication between the user and another party.

33 Claims, 19 Drawing Sheets

U.S. PATENT DOCUMENTS

| | | | |
|---|---|---|---|
| 5,724,580 | A | 3/1998 | Levin et al. |
| 5,833,623 | A | 11/1998 | Mann et al. |
| 5,899,855 | A | 5/1999 | Brown |
| 5,942,986 | A | 8/1999 | Shabot et al. |
| 5,987,519 | A | 11/1999 | Peifer et al. |
| 6,038,469 | A | 3/2000 | Karlsson et al. |
| 6,093,146 | A | 7/2000 | Filangeri |
| 6,102,856 | A | 8/2000 | Groff et al. |
| 6,154,668 | A | 11/2000 | Pedersen et al. |
| 6,168,563 | B1 | 1/2001 | Brown |
| 6,215,403 | B1 | 4/2001 | Chan et al. |
| 6,225,901 | B1 | 5/2001 | Kail, IV |
| 6,234,964 | B1 | 5/2001 | Iliff |
| 6,238,338 | B1 | 5/2001 | DeLuca et al. |
| 6,245,013 | B1 | 6/2001 | Minoz et al. |
| 6,254,536 | B1 | 7/2001 | DeVito |
| 6,278,999 | B1 | 8/2001 | Knapp |
| 6,292,698 | B1 | 9/2001 | Duffin et al. |
| 6,302,844 | B1 | 10/2001 | Walker et al. |
| 6,304,788 | B1 | 10/2001 | Eady et al. |
| 6,315,719 | B1 | 11/2001 | Rode et al. |
| 6,322,502 | B1 | 11/2001 | Schoenberg et al. |
| 6,398,728 | B1 | 6/2002 | Bardy |
| 6,406,426 | B1 | 6/2002 | Reuss |
| 6,424,860 | B1 | 7/2002 | Karlsson et al. |
| 6,442,433 | B1 | 8/2002 | Linberg |
| 6,638,218 | B2 | 10/2003 | Bulat |
| 6,804,656 | B1 | 10/2004 | Rosenfeld |
| 6,804,661 | B2 | 10/2004 | Cook |
| 6,893,396 | B2 | 5/2005 | Schulze et al. |
| 6,978,169 | B1 | 12/2005 | Guerra |
| 6,978,286 | B2 | 12/2005 | Francis et al. |
| 7,034,691 | B1 | 4/2006 | Rapaport et al. |
| 7,038,588 | B2 | 5/2006 | Boone |
| 7,079,177 | B2 * | 7/2006 | Okazaki et al. .......... 348/211.12 |
| 7,256,708 | B2 | 8/2007 | Rosenfeld |
| 7,287,031 | B1 | 10/2007 | Karpf et al. |
| 7,304,580 | B2 | 12/2007 | Sullivan et al. |
| 7,336,187 | B2 | 2/2008 | Hubbard, Jr. et al. |
| 7,411,510 | B1 * | 8/2008 | Nixon ............................ 600/301 |
| 2002/0177759 | A1 | 11/2002 | Schoenberg et al. |
| 2002/0196141 | A1 * | 12/2002 | Boone et al. ................... 340/540 |
| 2003/0023461 | A1 | 1/2003 | Quintanilla et al. |
| 2003/0061073 | A1 | 3/2003 | Seow et al. |
| 2004/0054261 | A1 * | 3/2004 | Kamataki et al. ............. 600/300 |
| 2004/0111296 | A1 | 6/2004 | Rosenfeld |
| 2004/0128163 | A1 | 7/2004 | Goodman et al. |
| 2005/0021369 | A1 | 1/2005 | Cohen et al. |
| 2005/0038326 | A1 * | 2/2005 | Mathur .......................... 600/300 |
| 2005/0101841 | A9 * | 5/2005 | Kaylor et al. .................. 600/300 |
| 2005/0159984 | A1 | 7/2005 | Hirano et al. |
| 2005/0197545 | A1 | 9/2005 | Hoggle |
| 2005/0209880 | A1 | 9/2005 | Drelicharz et al. |

OTHER PUBLICATIONS

Shabot, et al., "Wireless Clinical Alerts for Physiologic, Laboratory and Medication Data," Departments of Enterprise Information Services, Surgery and Pharmacy Cedars-Sinai Health System, Los Angeles, California.

Dumer, et al., "Remote Medical Evaluation and Diagnostics (RMED)—A Testbed for Hypertensive Patient Monitoring," U.S. Army Research Laboratory, Aberdeen Proving Ground, Maryland, Veterans Administration, St. Louis, Missouri.

Da Fonte, et al., "Abstract of Intelligent Management of Processes in an ICU Telemedicine System," Proceedings of the 22nd Annual Int'l Conf. of the IEEE Engineering in Medicine and Biology Society, IEEE Computer Society Press, Piscataway, NJ, pp. 2932-2935, http://tie.telemed.org/citations.asp?ID=10843.

Ramana Reddy PhD, "Secure Collaboration Technology for Rural Clinical Telemedicine—Final Report", Concurrent Engineering Research Center, West Virginia University, Morgantown, WV 26506-6506.

Reddy, et al., "Challenges to Physicians' Use of a Wireless Alert Pager," Informatics in Biology and Medicine, Information and Computer Science Department, University of CA, Irvine, USA, Departments of Surgery and Enterprise Information Systems, Cedars-Sinai Medical Center, Los Angeles, USA, FX Palo Alto Laboratory, Palo Alto, USA.

Breslow, Abstract of "ICU telemedicine. Organization and communication," Crit. Care. Clin., Oct. 2000, vol. 16, No. 4, pp. 707-722, x-xi, accessed at http://www.ncbi.nlm.nih.gov/ENTREZ/QUERY.FCGI?CMD=rETRIEVE&DB=pUBmED&LIST UIDS=11 ..., Mar. 23, 2005.

Abstract of "Project Overview," accessed at http://archive.dstc.edu.au/tardis/moreview.html, Mar. 23, 2005 (original publication date not provided).

Reddy, et al., "Secure Collaborative Telemedicine in Rural West Virginia," Concurrent Engineering Research Center, West Virginia University, St. Mary's Hospital, Valley Health Systems, Inc., (publication date not provided).

Smith, "Critical care at the electronic frontier of the 21st Century: Report from the 29th Educational and Scientific Symposium of the Society of Critcal Care Medicine, Orlando, USA Feb. 11-15, 2000," Crit. Care, Mar. 15, 2000, vol. 4, Issue 2, pp. 101-103, www.ccforum.com/content/4/2/101.

Kofos, et al., "Telemedicine in Pediatric Transport: A Feasibility Study," Pediatrics, vol. 102, No. 5, Nov. 5, 1998, p. e58, http://pediatrics.aappublications.org/cgi/content/full/102/5/e58.

Collection of Abstracts, "E-Health", 17 pages.

Collection of Abstracts, "Systems—The role of telemedicine/telehealth in health care", 30 pages.

Project overview, accessed at http://archive.dstc.edu/tardis/moreview.html, Dec. 11, 2004 (original publication date not provided).

"Decision support system for telemedicine based on multiple expertise", The ACM Digital Library, CBMS archive, http://portal.acm.org/citation.cfm,?id=791224.792005&col1=ACM&dl=ACM&CFID=1515... accessed on Jan. 22, 2007.

Ruffino, "Using a Pocket PC to Implement Telemedicine for Homecare," Symposium on Applications and the Internet Workshops, 2001, p. 1.

Lee, "Intensivist Staffing in Intensive Care Units (ICUs)," Academy Health Research Syntheses, pp. 1-12 (publication date not provided).

Bates, et al., "Reducing the Frequency of Errors in Medicine Using Information Technology," J Am Med Inform Assoc., 2001, vol. 8, pp. 299-308, www.iamia.org/cgi/content/full/8/4/299?maxtoshow=&HITS=10&hits=10&RESUL, Nov. 5, 2004.

"Wireless System to Track Vital Signs," The Business Ledger Online, Jun. 2001, Archives, p. 1-2, accessed at web site www.thebusinessledger.com, www.ncbl.com/archive/06-01healthcare.html, Dec. 11, 2004.

"Improvements to National Defense System," High Tech Maui Online, Winter 2000/2001, p. 1-4, www.hightechmaul.com.

Field, et al., "Telemedicine and Remote Patient Monitoring," (reprinted) J Am MedAssoc., Jul. 24-31, 2002, vol. 288, No. 4, pp. 423-425.

Bates, "The Quality Case for Information Technology in Healthcare," BMC Med Inform Decis Mak., 2002, vol. 2, No. 7, pp. 1-21 (published online Oct. 23, 2002).

Fischer, et al., "Handheld Computing in Medicine," Nov. 26, 2002, www.iamia.org/egi/content/full/10/2/139?maxtoshow=&HITS=10&hits=10&RESUL.

Major, et al., "Wireless Clinical Alerts and Patient Outcomes in the Surgical Intensive Care Unit," The American Surgeon, Dec. 2002, vol. 68, p. 1057-1060.

"Drivers of Broadband in Health," Information Economy Online, 2002, p. 1-6, accessed at web site www2.dcita.gov.au/ie/publications/2002/08/bb-health/drivers, Nov. 26, 2004.

"SICS Audit Groups—Highlights of Annual Audit Meeting 2002, 2001, 2000," accessed at web site www.scottishintensivecare.org.uk/sicsag-meetings.htm, Oct. 25, 2004 (original publication date note provided).

Fitzpatrick, "Connecting Families, Clinicians and Extended Social Networks," SIG CHI Conference Paper, accessed at web site www.informatics.sussex.ac.uk/interact/publications/geraldineCHI2004.pdf, Nov. 26, 2004, (original publication date not provided).

Jacobus, "The Billing, Cost, and Outcome Benefits from Remote Patient Monitoring," Cybernet Medical, p. 1-21, accessed at web site www.cybernetmedical.com/media/papers/The%20cost%20and%20outcome%20benefits.pdf, Nov. 26, 2004 (original publication date not provided).

Chen, et al., "PalmCIS: A Wireless Handheld Application for Satisfying Clinician Information Needs," J Am Med Inform Assoc., 2004, vol. 11, pp. 19-28 (first published Oct. 5, 2003 as JAMIA PrePrint; doi:10.1197/jamia.M1387), www.iamia.org/cgi/content/full/11/1/19?maxtoshow=&HITS=10&hits=10&RESUL.

Martin, "Remote Access to Medical Specialists (RAMS)—Remote Patient Care Monitoring Test Bed," Final Report, Oct. 2003, p. 1-14.

Marcin, et al., "Use of Telemedicine to Provide Pediatric Critical Care Inpatient Consultations to Underdeserved Rural Northern California," J. Pediatr, 2004, vol. 194, pp. 375-380.

"State Releases Report Showing Health IT Can Potentially Save $2.48 Billion," ATSP Online, pp. 1-3, accessed at web site www.atsp.org/news/research.asp?contentID=1497&FullStory=, Oct. 21, 2004 (original publication date not provided).

Gardner, et al., "Using Computer Technology to Detect, Measure, and Prevent Adverse Drug Events," J. Am Med Inform Assoc., 2004, vol. 11, pp. 535-536 (first published Aug. 18, 2004 as JAMIA PrePrint; doi:10.1197/jamia.M1651), www.iamia.org/cgi/content/full/11/6/535?maxtoshow=&HITS=10&hits=10&RESUL.

"Trauma ICU System," Vanderbilt University Online, accessed at [web site], Oct. 27, 2004 (original publication date not provided), http://simon.project.vanderbilt.edu/ICUSystem.htm.

"Architecture," Vanderbilt University Online, accessed at web site http://milo.vusc.vanderbilt.edu/Architecture.htm, Oct. 27, 2004 (original publication date not provided).

Nuccio, "Telemedicine: The Future is Now," J. Respir. Care Pract., Sep. 2004, accessed at web site www.rtmagazine.com(article.php?s=RT/2004/09&p=1, Oct. 24, 2004 (original publication date not provided).

"Benefits Realized for Selected Health Care Functions," Healthcare Information and Management Systems Society Online, Nov. 10, 2004, p. 1.

"Telemedicine in Other Countries," Ingegneria Bomedica Online, accessed at web site www.ingbiomedica.unina.it/teleplans-doc/wp4_0041_5.htm, Nov. 26, 2004, p. 1-43 (original publication date not provided).

"Virtual Critical Care Unit (ViCCU)," ICT Centre Online, accessed at web site www3.ict.csiro.au/ict/content/display/0,,a16254_b16412_d41654,00.html, Nov. 26, 2004, p. 1-2 (original publication date not provided).

"S52 Critical Care Systems," AMAI 2001 Symposium—Schedule Detail, AMIA Online, accessed at www.amia.org/online html/S52.htm, Oct. 22, 2004, pp. 1-8 (original publication date not provided).

Grundy, et al., "Telemedicine in Critical Care: An Experiment in Health Care Delivery," JACEP, vol. 6, pp. 439-444, Oct. 1977.

Johnson, et al., "A computerized Alert Program for Acutely Ill Patients," Jour. Nursing Admin., Jun. 1980, pp. 26-35.

Grundy, et al., "Telemedicine in Critical Care: Problems in Design, Implementation, and Assessment," Critical Care Medicine, vol. 10, No. 7, pp. 471-475, Jul. 1982, published in U.S.A.

Shabot, et al., "Automatic Extraction of Intensity—Intervention Scores From a Computerized Surgical Intensive Case Unit Flow sheet," Chpt. 17, pp. 266-276.

deLima, et al., "Successful Implementation of a Multiple—ICU Clinical Information System in a Tertiary Care Medical Centers", 1988.

Brown, et al., "Effect on ICU mortality of a full-time critical care specialist," Chest, vol. 96, pp. 127-129, 1989, accessed at web site www.chestjournal.org/cgi/content/abstract/96/1/127, Dec. 11, 2004.

"Monitoring Equipment lays path for step-down units—Non-Invasive Monitoring Systems Inc.'s Respiratory Monitor System," Health Industry Today, Dec. 1990, accessed at web site www.findarticles.com/p/articles/mi_m3498/is_n12_v53/ai_9295646/print, 1/4, 2005.

Kuperman, et al., "HELP: A Dynamic Hospital Information System," Chpts. 1-35, apps. A-D, Springer-Verlag, New York, Berlin, Heidelberg, London, Paris, Tokyo, Hong Kong, Barcelona, Budapest.

Gardner, et al., "Computerized Medical Care: The HELP System at LDS Hospital," J. Ahima, Jun. 1992, vol. 63, No. 6, pp. 68-78.

Gardner, et al., "Evaluation of User Acceptance of a Clinical Expert System," Jun. 24, 1994.

Haug, et al., "Decision Support in Medicine: Examples From the HELP System," Comp. and Biomed. Research, vol. 27, pp. 396-418, 1994.

Johnson, et al., "Discern—An Integrated Prospective Decision Support System," pp. 1-13, 1994.

"Intensive Care by Telemedicine a World First," The Australian, Nov. 14, 1995, accessed at web site http://archive.dstc.edu.au/tardis/media.html, Jul. 13, 2004.

Tate, et al., "Nurses, Pagers, and Patient-Specific Criteria: Three Keys to Improved Critical Value Reporting," pp. 164-168, © 1995.

Gardner, et al., "Computers in the Intensive Care Unit: A Match Meant to Be!" Textbook of Critical Care, 3d. Edition, © 1995, Chpt. 196, pp. 1757-1770.

Hales, et al., "Factors Impacting the Success of Computerized Preadmission Screening" pp. 728-732, © 1995.

Carlson, et al., "Does a Full-Time 24-hour Intrensivist Improve Care and Efficiency?," Critical Care Clinics, vol. 12, No. 3, Jul. 1996; pp. 525-551.

Report from House of Representatives Standing Committee on Family and Community Affairs regarding Health Information Management and Telemedicine, Sep. 20, 1996, pp. 109-239.

White, et al., "Case in Point: Automating the Bedside," Healthcare Informaties Online, nursing systems '97, accessed at web site www.healthcare-informatics.com/issues/1997/02-97/white.htm, Oct. 20, 2004.

"Secure Collaboration Technology for Rural Clinical Telemedicine—Phase 1 Quarterly Report Apr. 1-Jun. 30, 1997," West Virginia University Online, accessed at web site www.cerc.wvu.edu/n1m/telemedicine/project_reports/p193.html, Nov. 26, 2004.

Manders, et al., "Design of a Dynamically Reconfigurable Critical Care Monitor," Technical Report: ECE-97-01, May 1, 1997, accessed at web site http://simon.project.vanderbilt.edu/pub/embs97/p.html, Oct. 27, 2004.

Sima, et al., "Vital Signs Services for Secure Telemedicine Applications", Concurrent Engineering Research Center, West Virginia University, Morgantown, WV 26506-6506.

Balch, et al., "Telemedicine Expanding the Scope of Health Care Information," JAMIA, vol. 4, No. 1, Jan./Feb. 1997, pp. 1-5.

Kaplan, et al., "Designing Support for Remote Intensive-Care Telehealth Using the Locales Framework," pp. 173-184, © 1997.

Schneider, "Surfing the ICU," Healthcare Informatics Online, Aug. 1997, accessed at web site www.healthcare-informatics.com/issues/1997/08 97/net.htm, Dec. 11, 2004.

Lee, et al., "Remote Patient Monitoring Service through World-Wide Web," Proceedings—19th Int'l Conference—IEEE/EMBS, Oct. 30-Nov. 2, 1997, Chicago, IL U.S.A., pp. 928-931.

Evans, et al., "A Computer-Assisted Management Program for Antibiotics and Other Antiinfective Agents," New England Journal of Medicine, vol. 338, No. 4, Jan. 22, 1998, pp. 232-238.

Multz, et al., "A 'Closed' Medical Intensive Care Unit (MICU) Improves Resource Utilization When Compared with an 'Open' MICU," Am. J. Respir. Crit-Care Med., vol. 157, No. 5, May 1998, pp. 1468-1473, accessed at web site http://ajrccm.atsjournals.org/cgi/content/full/157/5/1468, Dec. 11, 2004.

Gardner, et al., "The HELP Hospital Information System: Update 1998," Int'l J. of Med. Informatics, vol. 54, 1999, pp. 169-182.

"Creating Safety Systems in Health Care Organizations," Excerpt from "To Err is Human: Building a Safer Health System," The Institute of Medicine, 1999.

Da Fonte, et al., Abstract of "A Prototype of Intelligent Telemedicine System in Intensive Care Units," Proceedings of the Seventeenth IASTED Int'l Conf., pub. by ACTA Press, Anaheim, CA, pp. 330-332, accessed at web site http://tie.telemed.org/citations2.asp?citation=7870&key=8954520126&page=1&pagecount=10, Oct. 21, 2004.

Schoenberg, et al., "Making ICU Alarms Meaningful: A Comparison of Traditional vs. Trend-Based Algorithms," AMIA '99 Annual Symposium.

Nadarajah, "Search for Strategies to Bring Australians Together," Healthcare Informatics Online, Jul. 2000, accessed at web site www.healthcare-informatics.com/issues/2000/07-00/international.htm, Nov. 26, 2004.

"IC-USA Changes Names to VISICU," Business Wire Online, Oct. 17, 2000, accessed at web site www.findarticles.com/p/articles/mi_M0EIN/is_2000_$_{Oct\_}$17/ai_66160840, Oct. 22, 2004.

Seiver, "ICU Bedside Technology—Critical Care Computing Past, Present, and Future," Crit. Care Clinics, vol. 16, No. 4, Oct. 2000, accessed at http://home.mdconsult.com/das/article/body/32326974.2/jorg=journal&source=&sp=115... Oct. 13, 2004.

Brief description of "Secure Collaboration Technology for Rural Clinical Telemedicine," Investigation Team led by Ramana, Reddy, accessed at web site www.scienceofcollaboratories.org/Resources/collab.php?177, Nov. 26, 2004, (original publication date not provided).

Breslow, Abstract of "ICU telemedicine. Organization and communication," Crit. Care. Clin., Oct. 2000, vol. 16, No. 4, pp. 707-722, x-xi, accessed at http://www.ncbi.nlm.nih.gov/ENTREZ/QUERY.FCGI?CMD=rETRIEVE&DB=pUBmED&LIST UIDS=11..., Mar. 23, 2005.

Smith, "Critical care at the electronic frontier of the 21st Century: Report from the 29th Educational and Scientific Symposium of the Society of Critical Care Medicine, Orlando, USA Feb. 11-15, 2000," Crit. Care, Mar. 15, 2000, vol. 4, Issue 2, pp. 101-103, www.ccforum.com/content/4/2/101.

Kofos, et al., "Telemedicine in Pediatric Transport: A Feasibility Study," Pediatrics, vol. 102, No. 5, Nov. 5, 1998, p. e58, http://pediatrics.aappublications.org/cgi/content/ful1/102/5/e58.

Agroyannis, et al., Abstract of "Telemedicine technology and applications for home hemodialysis" International Journal of Artificial Organs, Oct. 1999, vol. 22, No. 10, pp. 679-683.

Sittig, Abstract of "Potential impact of advanced clinical information technology on healthcare in 2015," Medinfo., 2004, vol. 2004, pp. 1379-1382.

J. Lee, "Intensivist Staffing in Intensive Care Units (ICUs)," Research Synthesis, Academy Health, Oct. 2002, http://www.academyhealth.org/syntheses/icu.htm, accessed on Jan. 29, 2006.

S. Shafazand, H. Shigemitsu and AB Weinacker, "A brave new world: Remote intensive care unit care for the 21st century", Critical Care Medicine 28(12):3945-3946; Journal: Editorial Material, Dec. 2000, www.garfield.library.upenn.edu/histcomp/critical-care_74-04/node/3398.html.

* cited by examiner

DOE, JOHN - 123123 OPENED BY SMITH, JANE

TASK EDIT VIEW OPTIONS CURRENT ADD HELP

1018

1020

DOE, JOHN

AGE: 54 YEARS

COMPUTERIZED METHOD FOR ESTABLISHING A COMMUNICATION BETWEEN A BEDSIDE CARE LOCATION AND A REMOTE CARE LOCATION

CROSS-REFERENCE TO RELATED APPLICATIONS

This application is related by subject matter to the invention disclosed in the commonly assigned application U.S. application Ser. No. 11/024,383, filed on even date herewith, entitled "Computerized Method and System for Providing Alerts from a Multi-Patient Display".

STATEMENT REGARDING FEDERALLY SPONSORED RESEARCH OR DEVELOPMENT

Not Applicable.

TECHNICAL FIELD

The present invention relates to computing environments. More particularly, embodiments of the present invention relate to methods and systems for use in, e.g., a patient care computing environment, the methods and systems for outputting alerts from a multi-patient display. Further embodiments of the present invention relate to methods in, for instance, a patient care computing environment, for establishing a communication, e.g., an audio, video, or combined audio/video communication, between a bedside care location and a remote care location.

BACKGROUND OF THE INVENTION

In today's healthcare system, there are a number of patient care disciplines with a shortage of qualified care providers. For instance, intensivists specializing in the care of the critically ill are in high demand and short supply. Often times, particularly in rural care locations, specialists (e.g., intensivists) are not available on site to care for patients presenting with certain specialized ailments. As a result, remote or centralized care locations wherein one or more specialists may be located and equipped with the ability to monitor patients at one or more patient care locations have emerged in recent years.

Modem monitoring equipment has the ability to alert a bedside care provider when any number of monitored patient data elements falls outside of predefined parameters. However, when a patient is being monitored by a remotely located care provider, such provider may not be aware of the alerts in a timely fashion, if at all.

As such, a system and method for outputting alerts received at a bedside care location to a remote care location would be advantageous. Additionally, a method and system for establishing a direct communication link between a bedside care provider and a remote care provider, for instance, when an alert has been received in association with a patient at the bedside care location, would be advantageous and aid improving the quality of healthcare services delivered.

BRIEF SUMMARY OF THE INVENTION

Embodiments of the present invention provide methods for use in, e.g., a patient care computing environment, for establishing a communication between a bedside care location and a remote care location. In one embodiment, the method may include providing a multi-patient view having a plurality of selectable patient indicators and receiving an indication that one of the plurality of selectable patient indicators has been selected by a user. The user's selection of one of the plurality of selectable patient indicators may be indicative of a request for initiation of a communication between the user and another party.

In another embodiment, the method of the present invention may include displaying a view of an electronic record associated with a patient, e.g., an electronic medical record, the view having a selectable audio/video launch indicator, and receiving an indication that the selectable audio/video indicator has been selected by a user. The user's selection of the audio/video launch indicator may be indicative of a request for initiation of a communication between the user and another party.

Additionally, embodiments of the present invention provide computer systems and computer-readable media for performing the methods herein disclosed.

BRIEF DESCRIPTION OF THE SEVERAL VIEWS OF THE DRAWING

The present invention is described in detail below with reference to the attached drawing figures, wherein:

FIG. 3 is an illustrative screen display of an exemplary multi-patient display having a plurality of selectable patient indicators and a visual patient alert indicator in accordance with an embodiment of the present invention;

FIG. 4 is an illustrative screen display accessible by selection of the selectable patient indicator of FIG. 3 that is associated with the visual patient alert indicator showing a patient lab alert in accordance with an embodiment of the present invention;

FIG. 10 is an illustrative screen display showing a communication initiation option accessible by selecting one of the selectable patient indicators from the multi-patient display shown of FIG. 3 in accordance with an embodiment of the present invention;

FIG. 11 is an illustrative screen display portion showing a communication initiation option accessible from an electronic record associated with a patient in accordance with an embodiment of the present invention;

FIG. 12 is an illustrative screen display showing a status display accessible upon selection of the communication initiation option of FIG. 11 by a user at or near the bedside care location in accordance with an embodiment of the present invention;

FIG. 13 is an illustrative screen display showing a communication privacy preference display accessible by selection of the "Privacy" indicator of FIG. 12 in accordance with an embodiment of the present invention;

FIG. 14 is an illustrative screen display showing an updated status display indicating that privacy settings have been established in accordance with an embodiment of the present invention;

FIG. 17 is an illustrative screen display showing a communication privacy setting status display accessible upon selection of the "Connect" indicator of FIG. 16 in accordance with an embodiment of the present invention.

DETAILED DESCRIPTION OF THE INVENTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The present invention provides computerized methods and systems for use in, e.g., a patient care computing environment, for outputting alerts from a multi-patient display. The present invention further provides a computerized method in, for instance, a patient care computing environment for establishing a communication, e.g., an audio, video, or combined audio/video communication, between a bedside care location and a remote care location. An exemplary operating environment for the present invention is described below.

Figure 1:
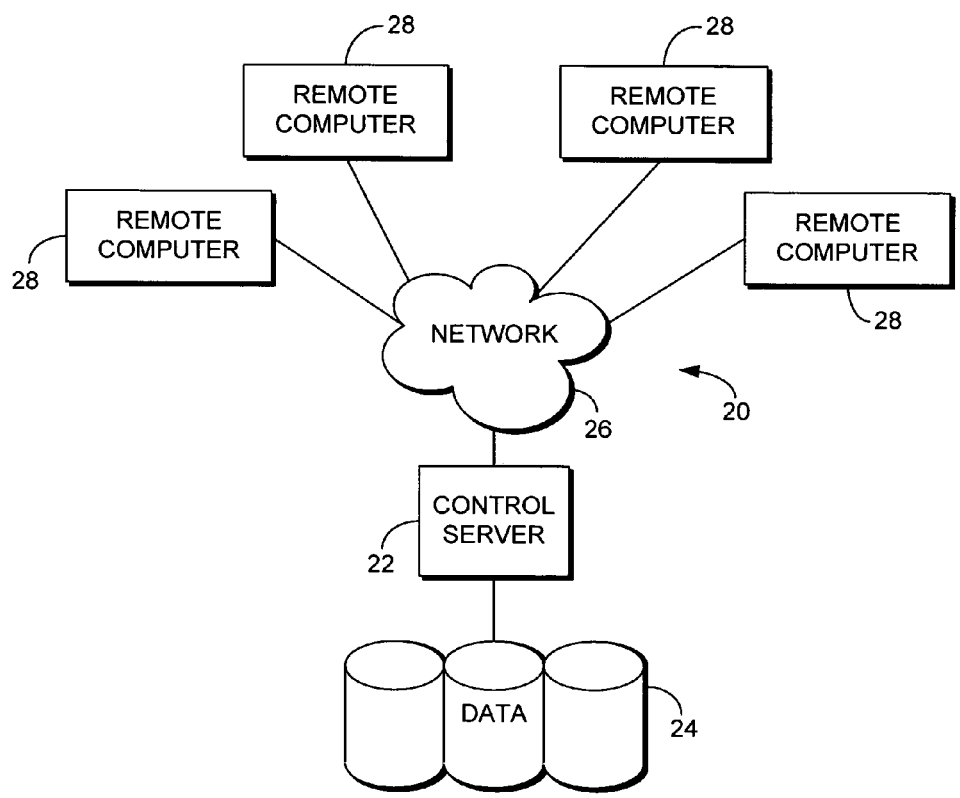
FIG. 1 is a block diagram of an exemplary computing system environment suitable for use in implementing the present invention.

Referring to the drawings in general, and initially to FIG. 1 in particular, an exemplary computing system environment, for instance, a medical information computing system, on which the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that may be accessed by control server 22, and includes volatile and nonvolatile media, as well as removable and nonremovable media. By way of example, and not limitation, computer-readable media may include computer storage media and communication media. Computer storage media may include, without limitation, volatile and nonvolatile media, as well as removable and nonremovable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by control server 22. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 24, provide storage of computer-readable instructions, data structures, program modules, and other data for control server 22.

The control server 22 may operate in a computer network 26 using logical connections to one or more remote computers 28. Remote computers 28 may be located at a variety of locations in a medical environment, for example, but not limited to, clinical laboratories, hospitals and other inpatient settings, ambulatory settings, medical billing and financial offices, hospital administration settings, home health care environments, and clinicians' offices. Clinicians may include, but are not limited to, a treating physician or physicians, specialists such as surgeons, radiologists and cardiologists, emergency medical technicians, physicians' assistants, nurse practitioners, nurses, nurses' aides, pharmacists, dieticians, microbiologists, and the like. Remote computers 28 may also be physically located in non-traditional medical care environments so that the entire health care community may be capable of integration on the network. Remote computers 28 may be personal computers, servers, routers, network PCs, peer devices, other common network nodes, or the like, and may include some or all of the elements described above in relation to the control server 22.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in the control server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a user may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like.

The control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Figure 2:
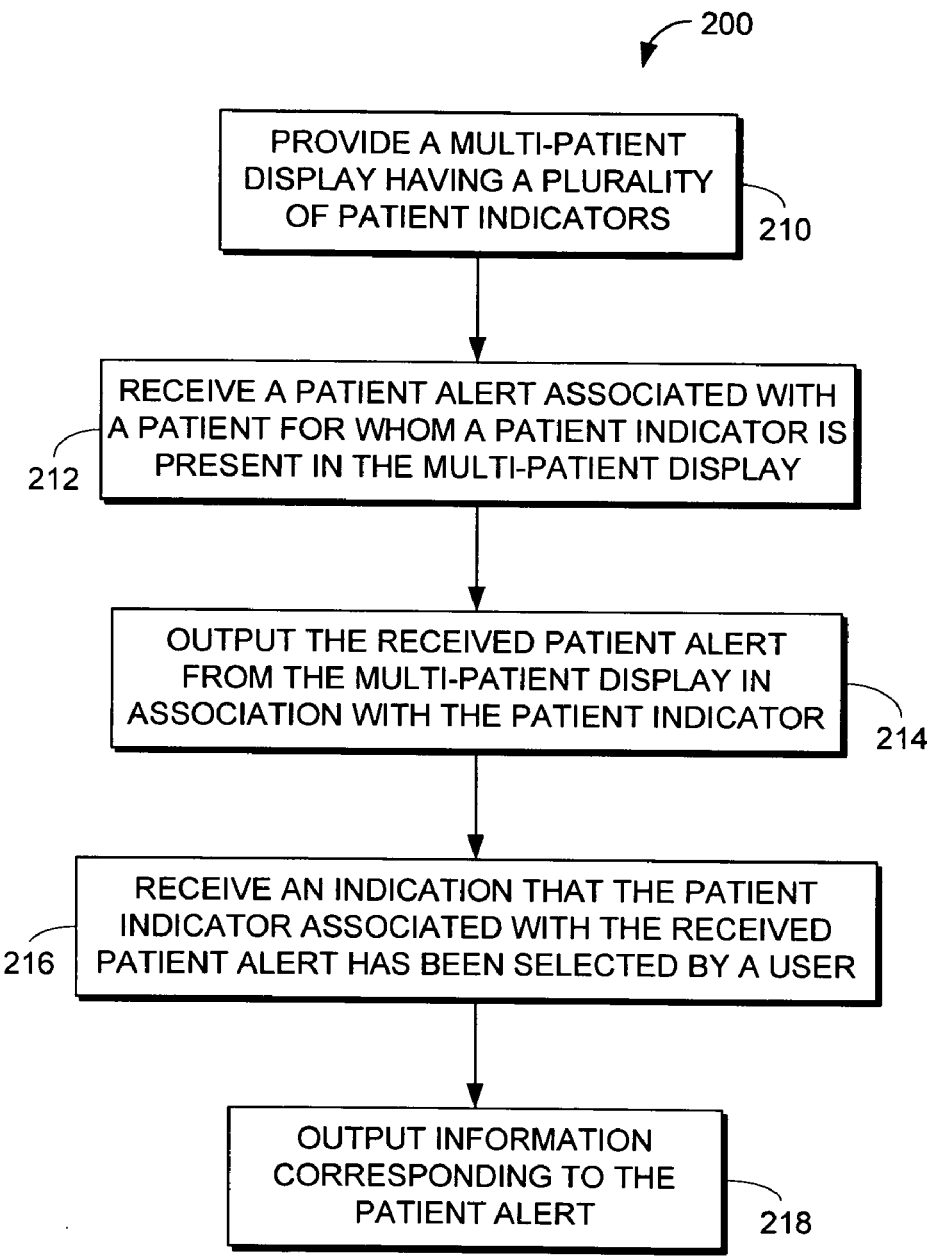
FIG. 2 is a flow chart representative of a computer program for outputting a patient alert from a multi-patient display in accordance with an embodiment of the present invention.

As previously mentioned, the present invention relates, in part, to a method for use in, e.g., a patient care computing environment, for outputting patient alerts from a multi-patient display. With reference to FIG. 2, a flow chart representative of a method for outputting alerts from a multi-patient display in accordance with an embodiment of the present invention is illustrated and depicted generally as reference numeral 200. Method 200 may be implemented on the above-described exemplary computing system environment (FIG. 1) and, by way of example only, may be utilized to output patient alerts from a multi-patient display viewable by an intensivist located centrally and/or remotely from one or more Intensive Care Units (ICUs) that he or she may be monitoring. (The terms "individual", "person", and "patient" are used interchangeably herein and are not meant to limit the nature of the reference individual in any way. Rather, the methods and systems described herein are equally applicable in, for instance, a veterinary setting. Further, use herein of the term "patient" is not meant to imply any particular relationship between the individual in question and those viewing the multi-patient display.)

Initially, as shown at block 210, a multi-patient display having a plurality of selectable patient indicators is provided. As used herein, the term "selectable patient indicators" refers to any selectable indicators, each of which is representative of a single patient care location, whether it be a patient room, a patient bed (of which there may be more than one in a single room), or the like.

Figure 3:
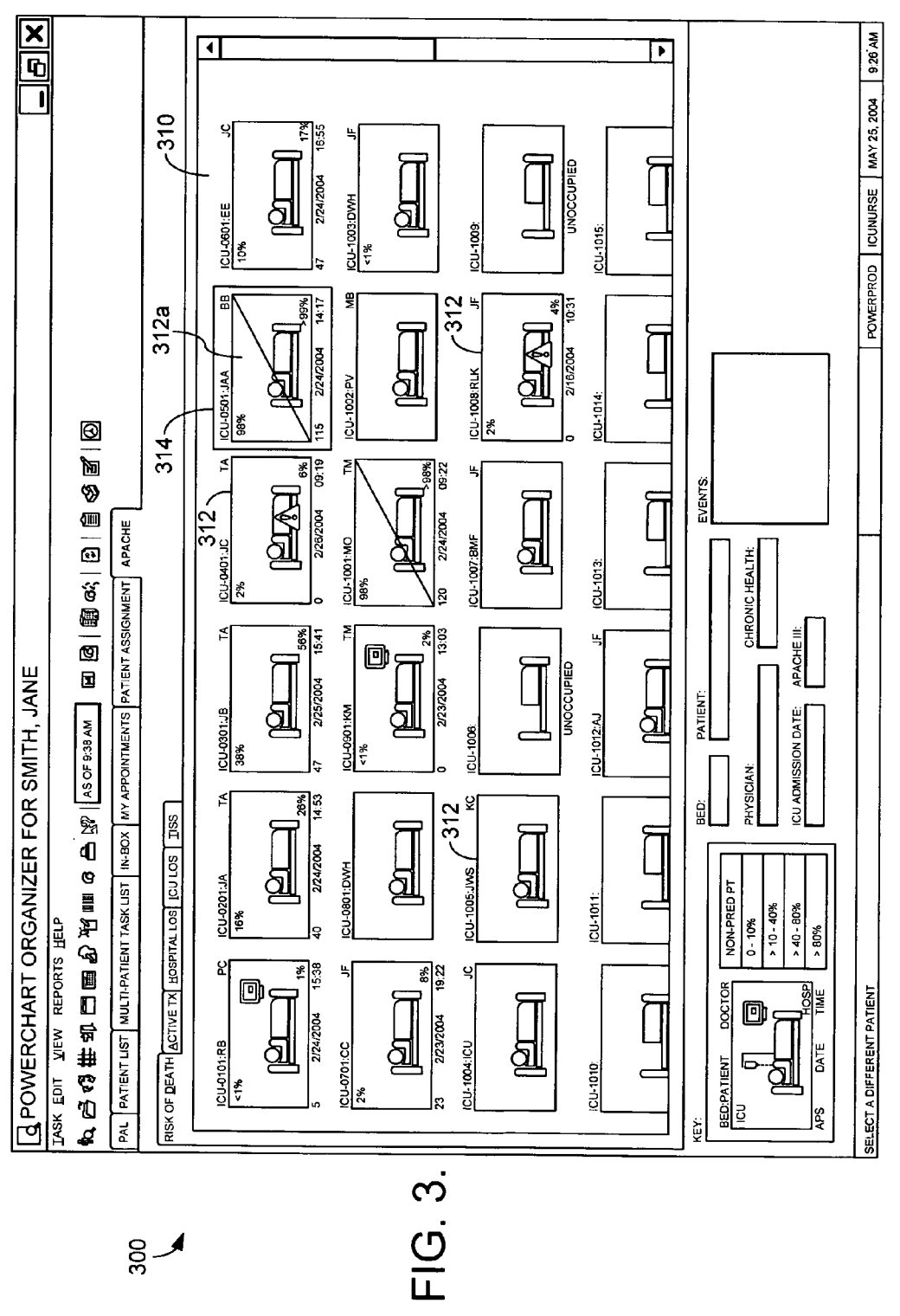

With reference to FIG. 3, an exemplary user interface having a multi-patient display area 310 is illustrated and designated generally as reference numeral 300. The multi-patient display area 310 of FIG. 3 includes a plurality of selectable patient indicators 312 each of which is representative of a single patient care location. Accordingly, whether or not a patient is assigned to a particular patient care location, each patient care location in the unit or area falling within the scope of the multi-patient display 310 has a selectable indicator with which it is associated. In the particular multi-patient display area 310 shown, not all patient care locations for which there is a selectable patient indicator 312 has a patient assigned thereto. Thus, for instance, the third row from the top, third patient indicator from the left, indicates that the corresponding patient care location is unoccupied. In this way, if a patient is assigned to a particular care location prior to such assignment information being input into the system, communication with the patient care location in question may still be established, as more fully described below.

A multi-patient display area 310 like the one shown in FIG. 3 is the APACHE

Bedboard available from Cerner Corporation of North Kansas City, Mo. In an embodiment, the selectable indicators of the APACHE Bedboard are color coded to indicate the risk of death for each patient based on the APACHE (Acute Physiology, and Chronic Health Evaluation) II prognostic scoring system. In another embodiment, the selectable indicators of the APACHE Bedboard indicate the predicted risk of active treatment and probability of discharge alive for each patient.

It will be understood and appreciated by those of ordinary skill in the art, however, that the multi-patient display area 310 shown in FIG. 3 is exemplary only and the particular layout is not intended to limit the scope of the present invention in any way. Any display area, or combination of display areas, having selectable indicators representative of a plurality of patient care locations may be utilized and all such variations are intended to be within the scope hereof.

With reference back to FIG. 2, the system subsequently receives a patient alert associated with a patient (in a particular patient care location) for which a selectable patient indicator is present in the multi-patient display, as shown at block 212. The patient alert received may be one or more of a critical patient alert, a single-parameter patient alert, a multi-parameter patient alert, or the like. Specific examples include trending alerts, ventilator weaning alerts and discharge alerts. Next, the system outputs the received patient alert from the multi-patient display in association with the patient indicator, as shown at block 214.

Referring back to FIG. 3, a visual patient alert indicator 314 is illustrated which indicates that a patient alert has been received corresponding to the patient in the patient care location represented by the selectable patient indicator in the top row, fifth from the left (i.e., ICU-0501). The visual patient alert indicator 314 shown is illustrated as a rectangular box surrounding the selectable patient indicator 312a associated with the patient care location from which an alert has been received. It will be understood by those of ordinary skill in the art that this is only one possible configuration for the visual patient alert indicator 314 and that many variations, for instance colored indicators, symbols, or the like, may be utilized and all such variations are intended to fall within the scope of the present invention. Additionally, an audible patient alert indicator may be output in conjunction with the visual patient alert indicator 314, if desired.

With reference back to FIG. 2, the system may subsequently receive an indication that the selectable patient indicator associated with the received patient alert has been selected by a user, for instance, an intensivist monitoring the multi-patient display from a location remote from the patient bed location or at any other location at which a number of patents may be monitored. This is shown at block 216. Upon receiving such indication, the system may output information corresponding to the patient alert received, as shown at block 218. The information corresponding to the patient alert received may include one or more components of information regarding the nature of the patient alert (e.g., a critical patient alert, a single-parameter patient alert, a multi-parameter patient alert, or the like) and the clinically appropriate response to the alert (e.g., "evaluate patient's condition immediately"). In addition to providing the components of information described, each alert may include one or more executable actions. For example, within the healthcare information technology system in which the system and method operate, a user may place a clinical order to address the alert, cancel an order in response to the alert or access reference material related to the alert. Also, if a user opts not to follow the alert, the user may document the reasoning upon selection of the action. In another example, a user may navigate to the data causing the alert to trigger. In a unified healthcare information technology system, by selecting an executable action, the user may be directed from the alert to the location of the data within a comprehensive electronic medical record. This allows the user to access immediately the data triggering the alert and the contextual clinical information relevant to the data triggering the alert.

In an embodiment, one or more executable action is displayed with the alert. For example, in addition to the acknowledgment button of the alerts in FIGS. 4-8, the alert may include buttons for initiating the executable actions related to the alerts.

In another embodiment, the visual patient alert indicator 314 may be a selectable indicator, selection of which causes the system to output information corresponding to the alert received, as described above with reference to the selectable patient indicators 312. This embodiment may be employed in conjunction with, or instead of, utilizing selectable patient indicators.

Figure 4:
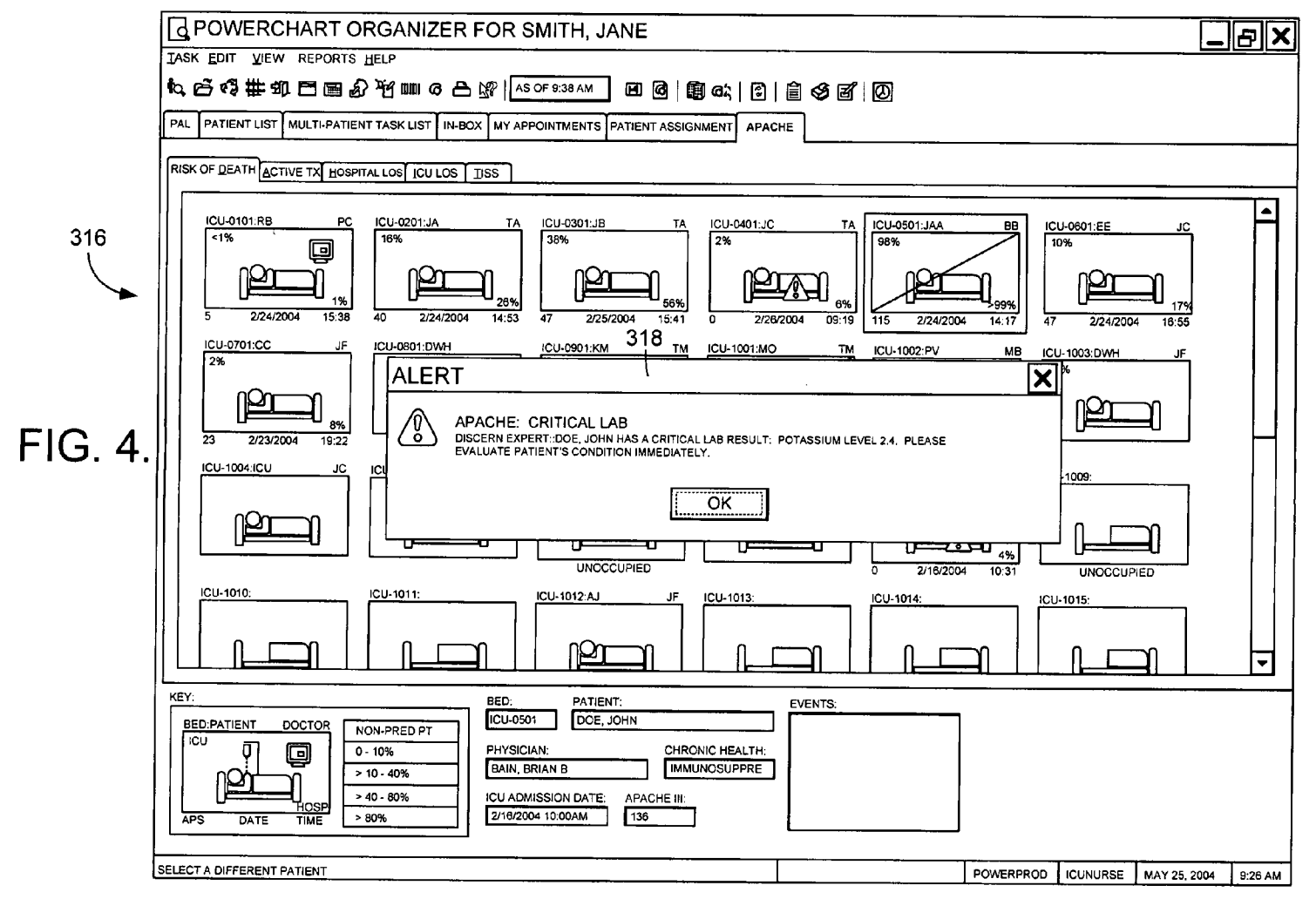
Figure 5:
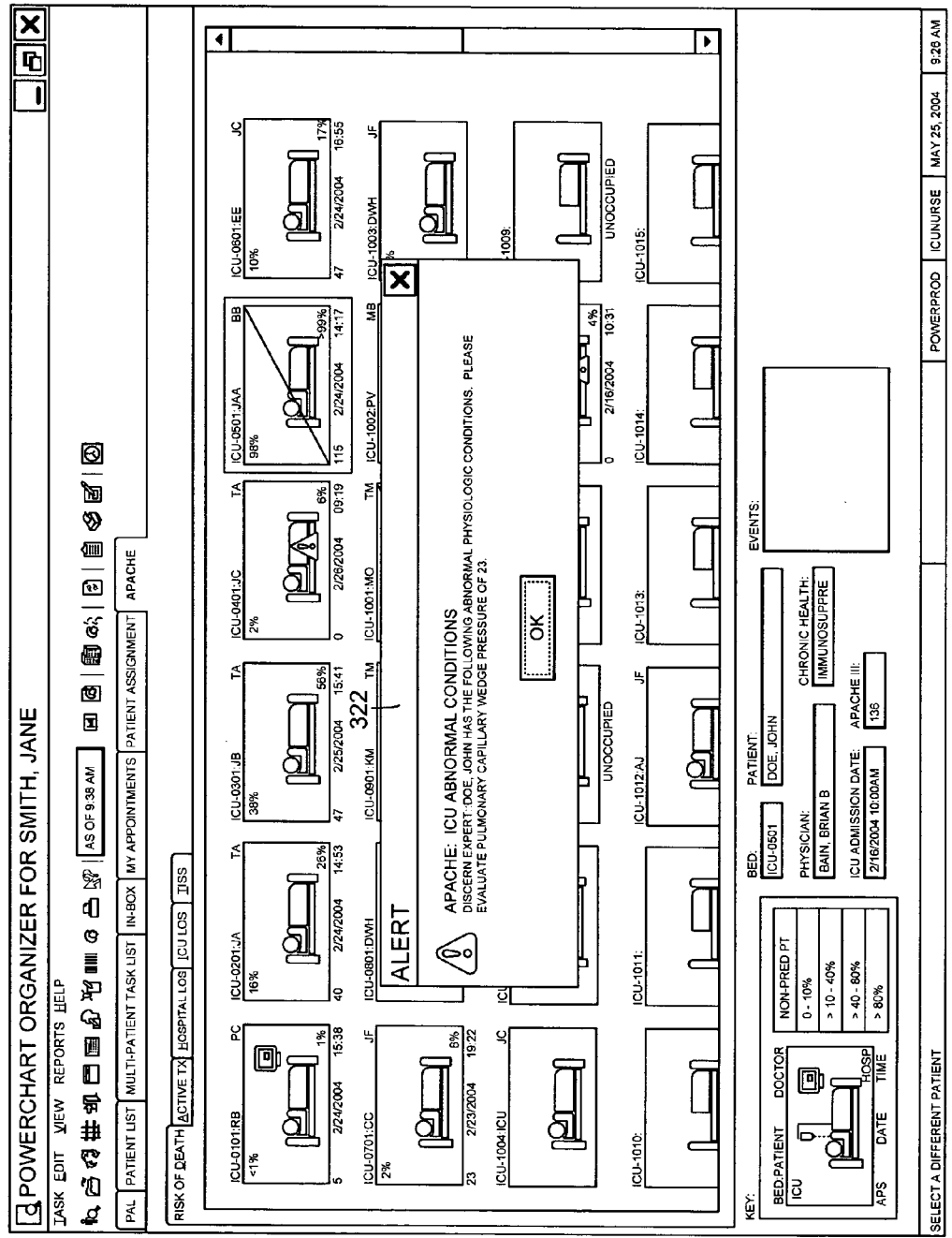
FIG. 5 is an illustrative screen display accessible by selection of the selectable patient indicator of FIG. 3 that is associated with the visual patient alert indicator showing an abnormal physiologic conditions alert in accordance with an embodiment of the present invention.

By way of example only, an exemplary screen display 316 is shown in FIG. 4 which is accessible upon selection of the selectable patient indicator 312a of FIG. 3 and includes a critical lab alert 318. FIG. 5 shows an exemplary screen display 320 accessible upon selection of the selectable patient indicator 312a having an abnormal physiologic conditions alert 322.

Figure 6:
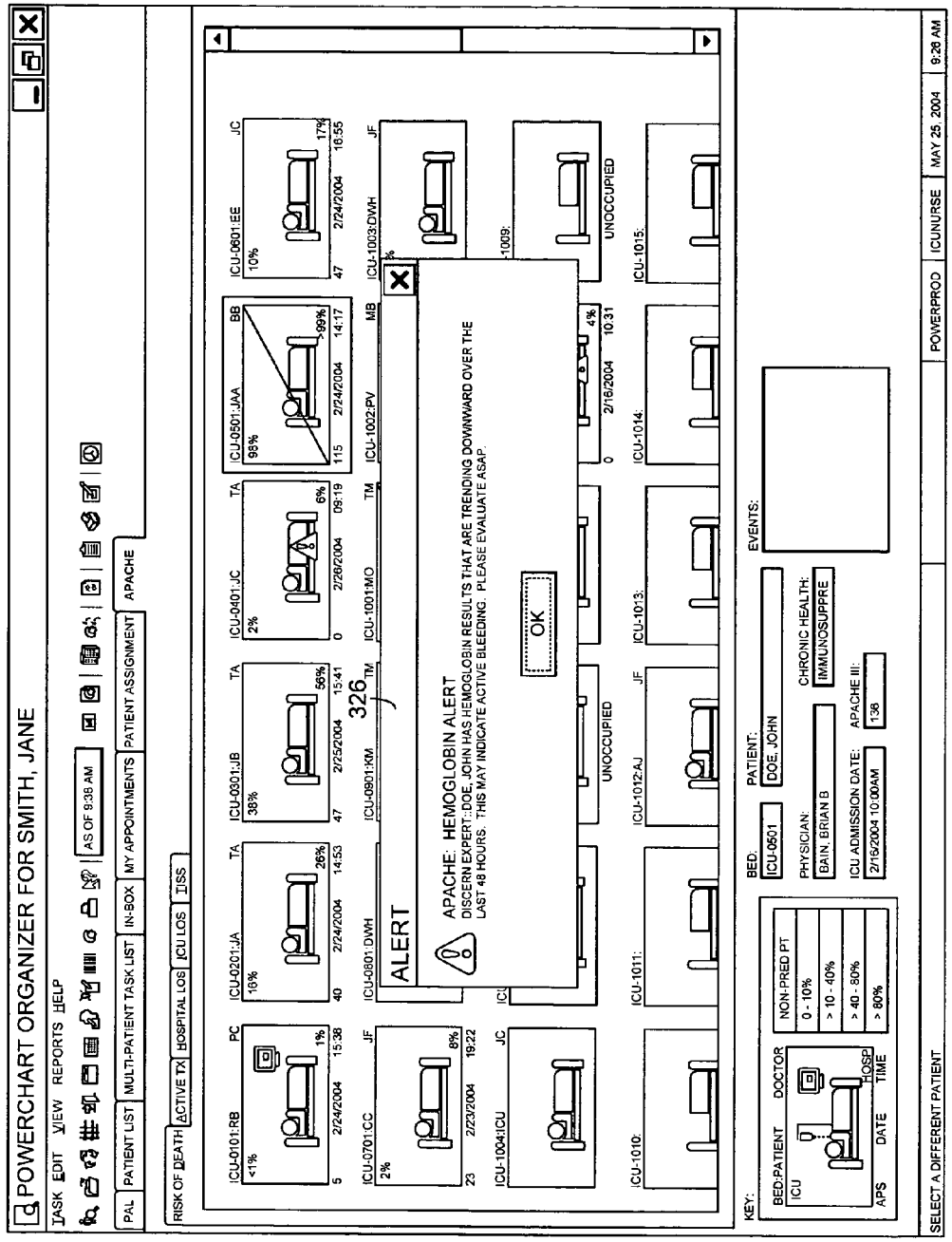
FIG. 6 is an illustrative screen display accessible by selection of the selectable patient indicator of FIG. 3 that is associated with the visual patient alert indicator showing a trending alert in accordance with an embodiment of the present invention.
Figure 7:
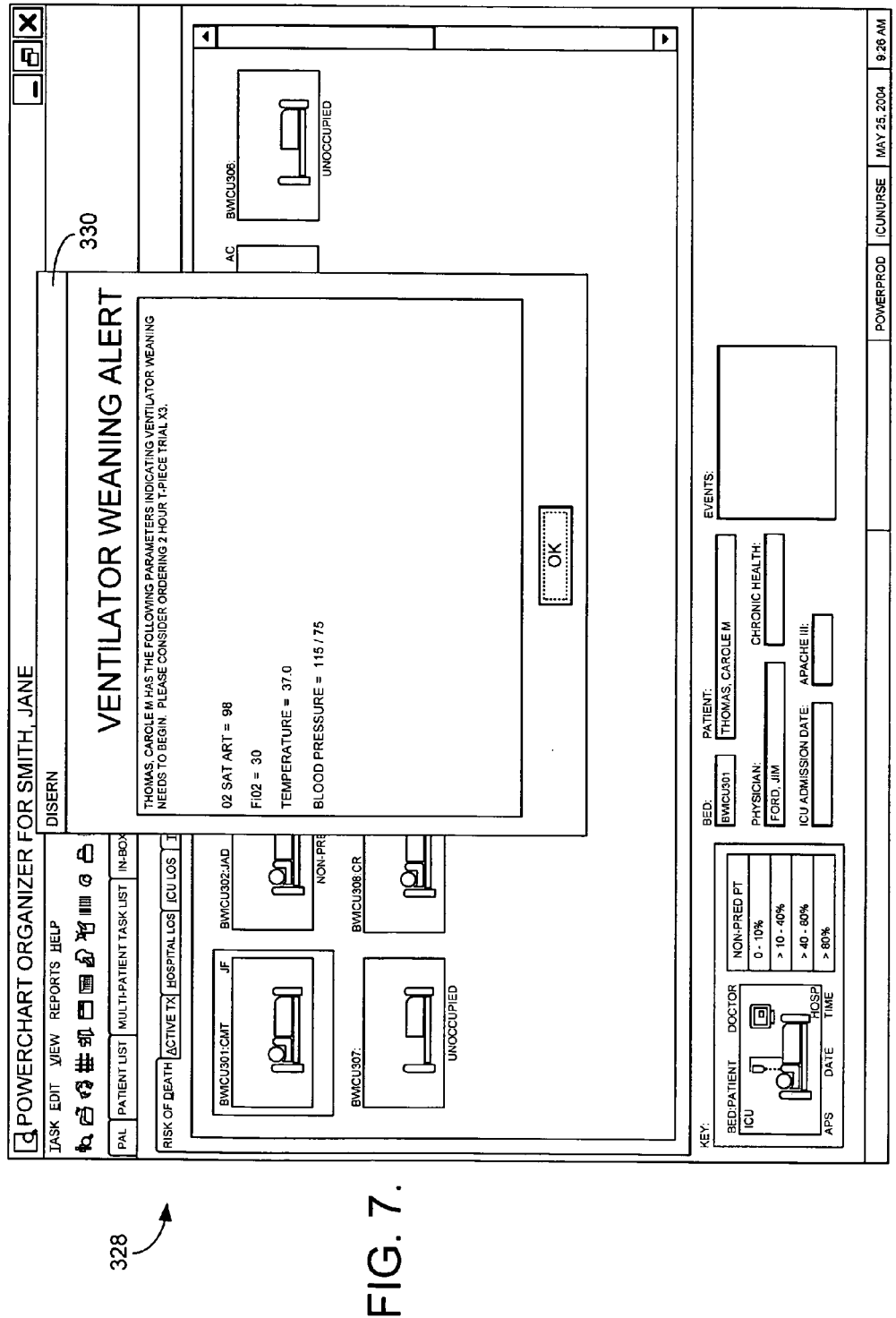
FIG. 7 is an illustrative screen display accessible by selection of the selectable patient indicator of FIG. 3 that is associated with the visual patient alert indicator showing a ventilator weaning alert in accordance with an embodiment of the present invention.
Figure 8:
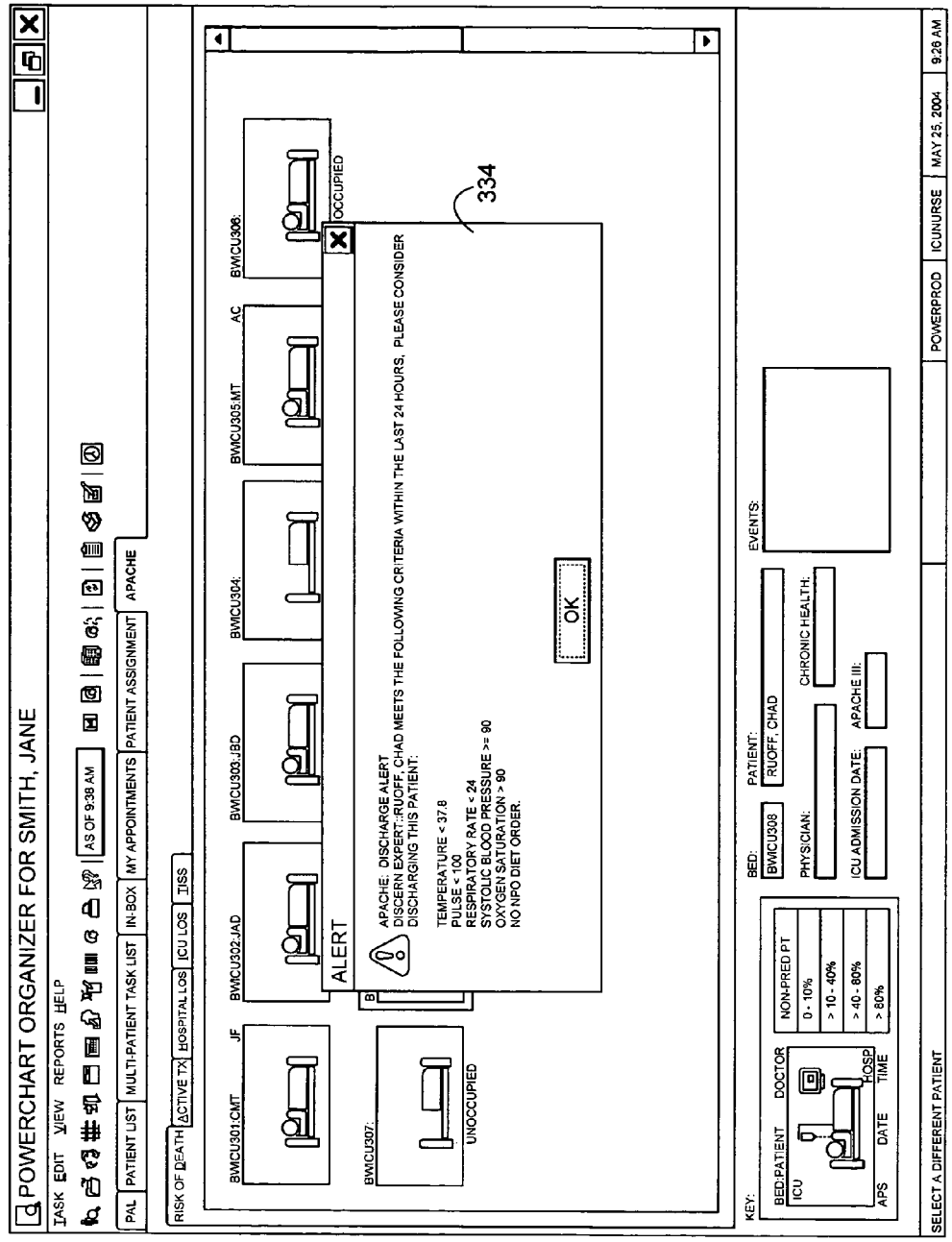
FIG. 8 is an illustrative screen display accessible by selection of the selectable patient indicator of FIG. 3 that is associated with the visual patient alert indicator showing a discharge alert in accordance with an embodiment of the present invention.

FIG. 6 shows an exemplary screen display 324 accessible upon selection of the selectable patient indicator 312a of FIG. 3 having a trending alert 326. Further, FIG. 7 shows an exemplary screen display 328 accessible upon selection of the selectable patient indicator 312a having a ventilator weaning alert 330. Additionally, FIG. 8 shows an exemplary screen display 332 accessible upon selection of the selectable patient indicator 312a of FIG. 3 having a discharge alert 334.

The alerts provide notice of a clinically notable condition or event that may require intervention. In addition to providing notice, each alert may be actionable. For example, a user may place a clinical order to address the alert, cancel an order in response to the alert or access reference material related to the alert. Also, if a user opts not to follow the alert, the user may document the reasoning from the displayed alert. In an embodiment, the actions are displayed within the alert. For example, in addition to the acknowledgment button of the alerts in FIGS. 4-8, the alert may include buttons for initiating actions related to the alerts.

Figure 9:
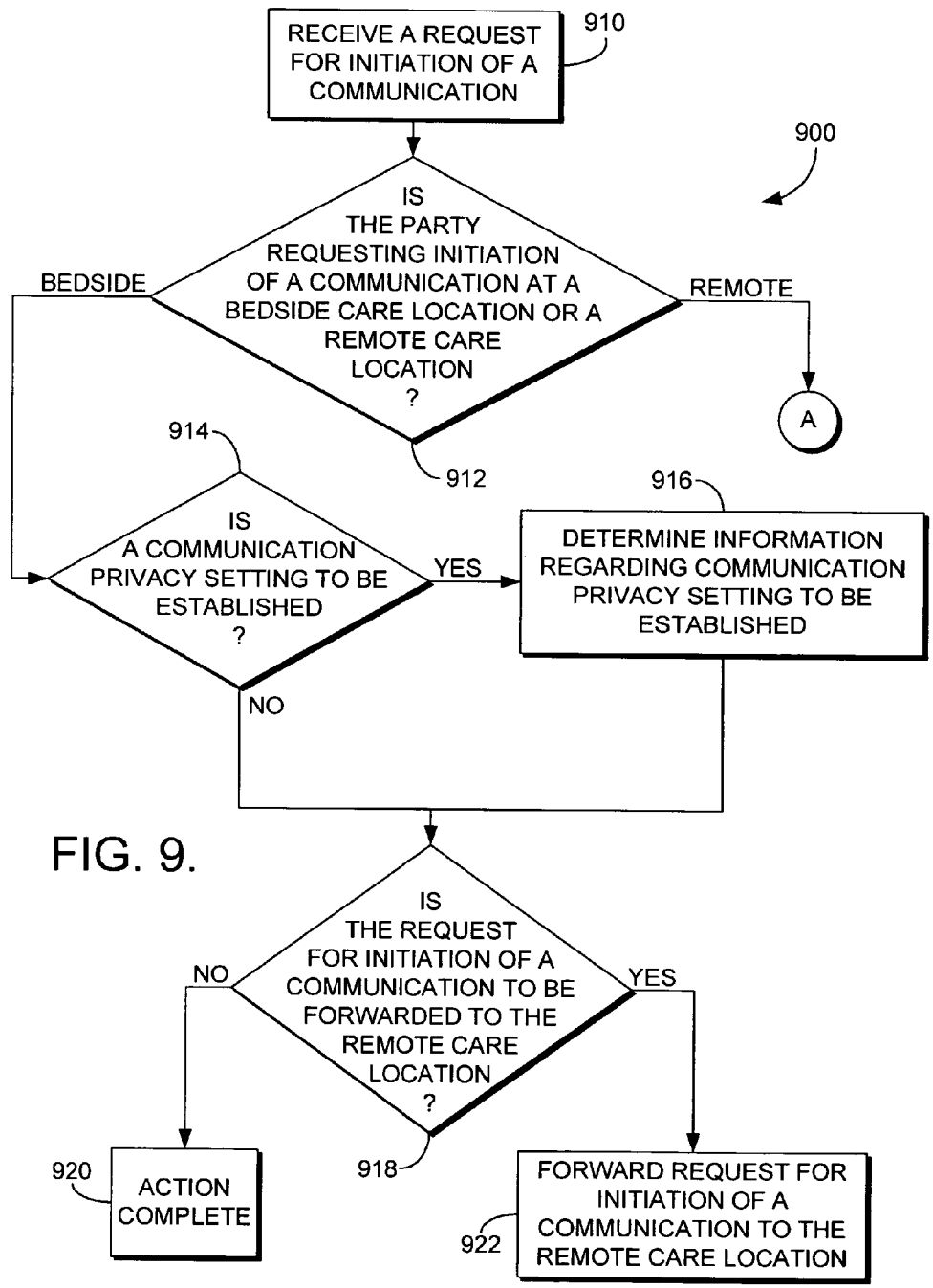
FIG. 9 is a flow chart representative of a computer program for establishing a communication between a bedside care location and remote care location in accordance with an embodiment of the present invention.
Figure 9:
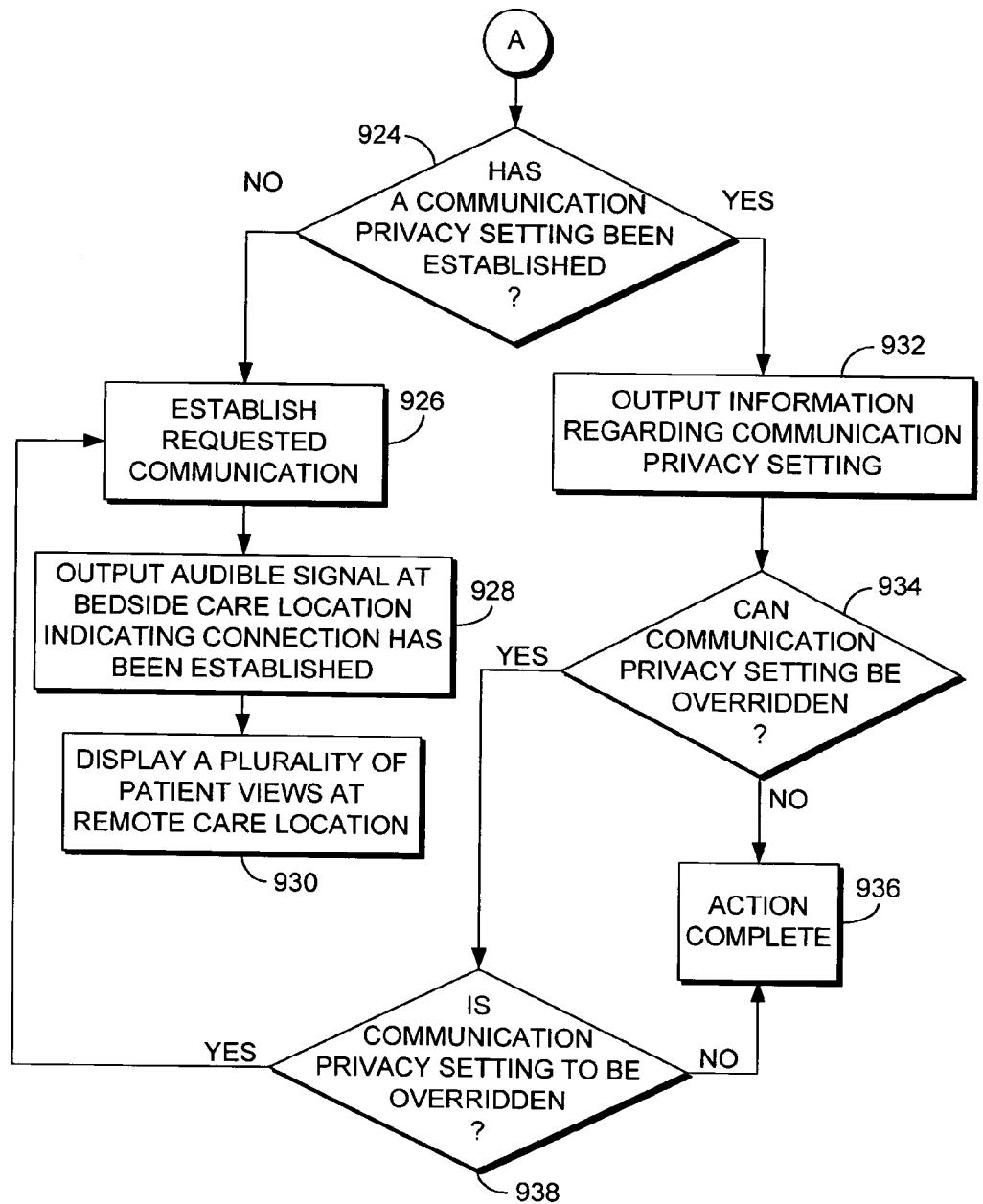

In another embodiment, the present invention relates to a computerized method and system for establishing a communication between a bedside care location and a remote care location. With reference to FIG. 9, a flow chart representative of a method for establishing such a communication in accordance with an embodiment of the present invention is illustrated and depicted generally as reference numeral 900. Method 900 may be implemented on the above-described exemplary computing system environment (FIG. 1) and, by way of example only, may be utilized to connect a user (e.g., a care provider) at a bedside care location to critical care resources when a patient condition requires those resources. More specifically, embodiments of the present invention may be utilized to permit a user at a remote or central care location to actively participate in, and/or direct the care of, critical patients through the use of direct audio, video, or audio/video communication with a user at a bedside care location. As used herein, a user at a "bedside care location" refers to a clinician (e.g., a physician or nurse practitioner) responsible for direction of patient care in, for instance, a critical care setting. This user also may be referred to as a "remote user" in that they may be remote to the bedside, unit, facility, or even city/state. As used herein, a user at a "bedside care location" refers to a care provider present at the patient bedside. By way of example only, this care provider may be, e.g., a nurse, respiratory therapist, a clinician, or the like.

Initially, as shown at block 910, the system receives a request for initiation of a communication, e.g., an audio communication, a video communication, or a combined audio/ video communication. That is, the system receives a request for initiation of a point-to-point audio connection which may be initiated independently of the video component, a point-to-point video connection which may be initiated independently of the audio component, or a combined point-to-point audio and video connection, as desired.

A request for initiation of a communication may be received upon a user's selection of one of a plurality of selectable patient indicators on a multi-patient view (e.g., the multi-patient display area 310 described hereinabove with reference to FIG. 3) or upon the user's selection of an audio/video initiation indicator associated with a patient's electronic record, e.g., a patient's electronic medical record. These two communication initiation options may be more fully understood with reference to FIGS. 10 and 11, respectively.

Figure 10:
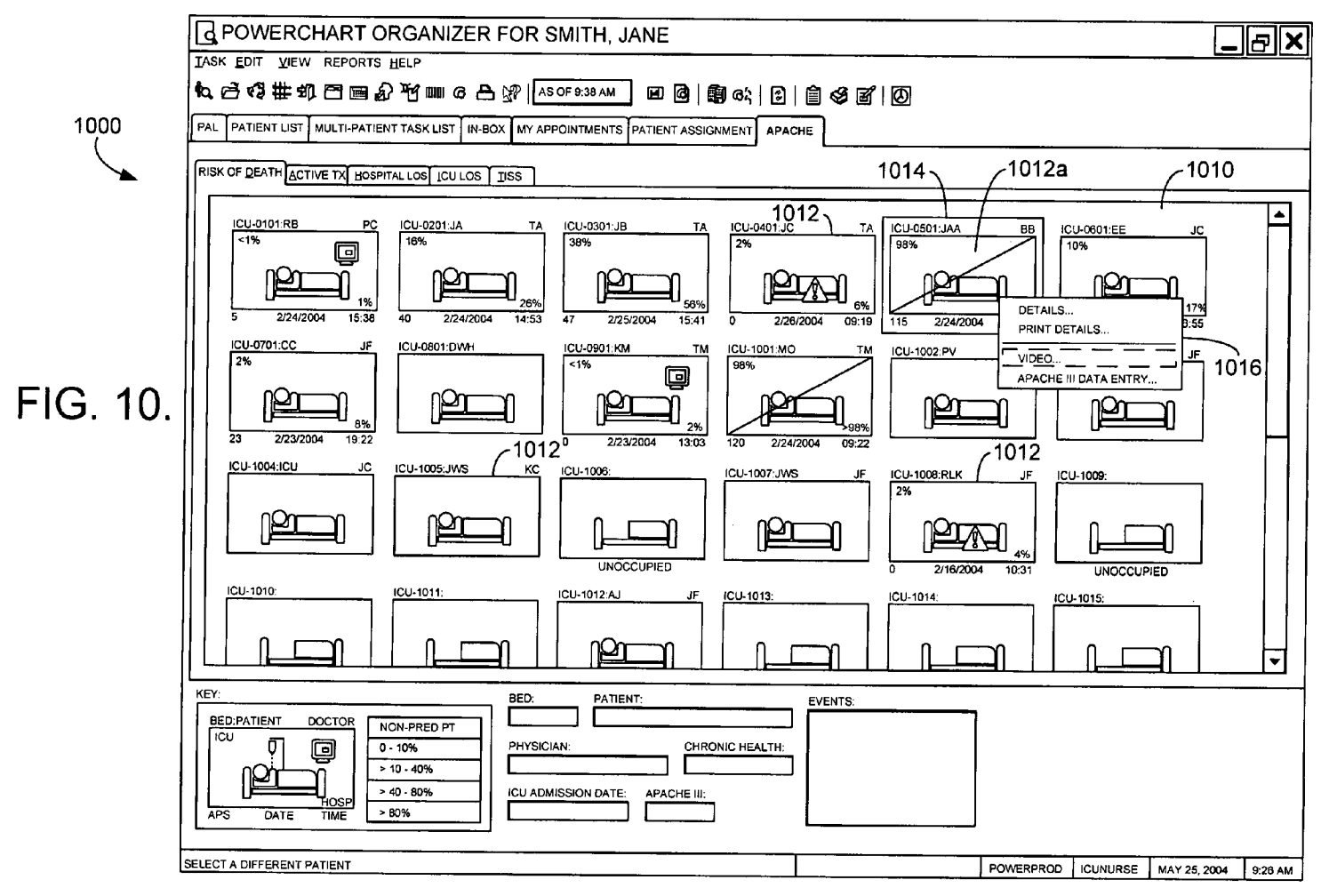

Referring to FIG. 10, an exemplary user interface having a multi-patient display area 1010 is illustrated and designated generally as reference numeral 1000. The multi-patient display area 1010 of FIG. 10 includes a plurality of selectable patient indicators 1012 each of which is representative of a single patient care location (as described hereinabove with reference to FIG. 3). The multi-patient display area 1010 further includes a visual patient alert indicator 1014 associated with the patient occupying the patient care location represented by the selectable patient indicator in the top row, fifth from the left (i.e., ICU-0501).

Contemplate a scenario wherein a user wishes to establish a communication with the patient and/or caregiver(s) in ICU-0501. In this instance, the user may select the selectable patient care indicator 1012a associated therewith. Subsequently, the user may be presented with an options menu 1016 having one or more selectable options thereon, one of which indicates that a communication may be established. In the options menu 1016 of FIG. 10, selection of the "Video . . . " indicator will initiate establishment of a communication in accordance with the location of the user, as more fully described below.

It will be understood and appreciated by those of ordinary skill in the art that the options menu 1016 illustrated in FIG. 10 and the selectable options shown in association therewith are exemplary only and that any number of options may be presented, selection of which may cause the system to initiate different functions. For instance, in addition to a selectable "Video . . . " indicator, the options menu 1016 may include a selectable "Audio . . . " indicator and/or a selectable "Audio/Video . . . " indicator, if desired. All such variations are contemplated to be within the scope hereof.

Referring to FIG. 11, a portion of an illustrative screen display is illustrated and designated generally as reference numeral 1018. The screen display 1018 illustrates a portion of an electronic record, e.g., an electronic medical record, associated with patient John Doe and includes a selectable audio/video initiation indicator 1020. Similar to a user's selection of the selectable "Video . . . " indicator of FIG. 10, selection of the audio/video initiation indicator 1020 of FIG. 11 will initiate establishment of a communication in accordance with the location of the user, as more fully described below.

Referring back to FIG. 9, once a request for initiation of a communication has been received, the system determines whether the party requesting initiation of the communication is making such request from a bedside care location or from a remote care location. This is shown at block 912. Such determination is made as, in the currently described embodiment, the options available to a user at bedside care location differ from those available to a user at a remote care location, as more fully described below. However, in the event the same options were given to each of a user at a bedside care location and a user at a remote care location, such determination would be unnecessary and may be eliminated from the illustrated method.

Though not intended to limit the scope of the present invention, it will be understood by those of ordinary skill in the art that a request for initiation of a communication from a bedside care location will typically be received upon selection of an audio/video initiation indicator associated with a patient's electronic record (e.g., audio/video initiation indicator 1020 of FIG. 11) and a request for initiation of a communication from a remote care location will typically be received upon selection of a selectable patient indicator shown on a multi-patient display area (e.g., selectable patient indicator 1012 of the multi-patient display area 1010 of FIG. 10).

In a currently preferred embodiment of the present invention, a user at a bedside care location may implement communication privacy settings in association with the establishment of a communication with the patient associated with the bedside care location in question. Temporary communication privacy settings, that is, communication privacy settings having a finite or defined duration, may be established if, for instance, the patient's family is visiting, the patient is undergoing a bedside procedure, the patient is sleeping, or the like. Alternatively, permanent communication privacy settings may be established in the event, for instance, the patient's religious or cultural philosophy does not permit them to be photographed or captured on video and/or audio. Thus, if it is determined that the user is located at a bedside care location, the system next determines whether a communication privacy setting is to be established. This is indicated at block 914.

If it is determined that a communication privacy setting is to be established, the system subsequently determines information regarding the desired setting, as indicated at block 916. In one embodiment, the system receives input from the user at the bedside care location regarding one or more of the nature of the communication privacy setting to be established (i.e., temporary or permanent), a duration of the communication privacy setting to be established (if the nature thereof is temporary), a reason for the communication privacy setting (e.g., "religious preference" or "undergoing bedside procedure"), and an indication whether the communication is capable of being overridden by a user in a remote care location (as more fully described below). (It should be noted that a communication privacy setting may be modified or removed from association with a particular patient care location using the method and system of the present invention as well.)

Figure 12:
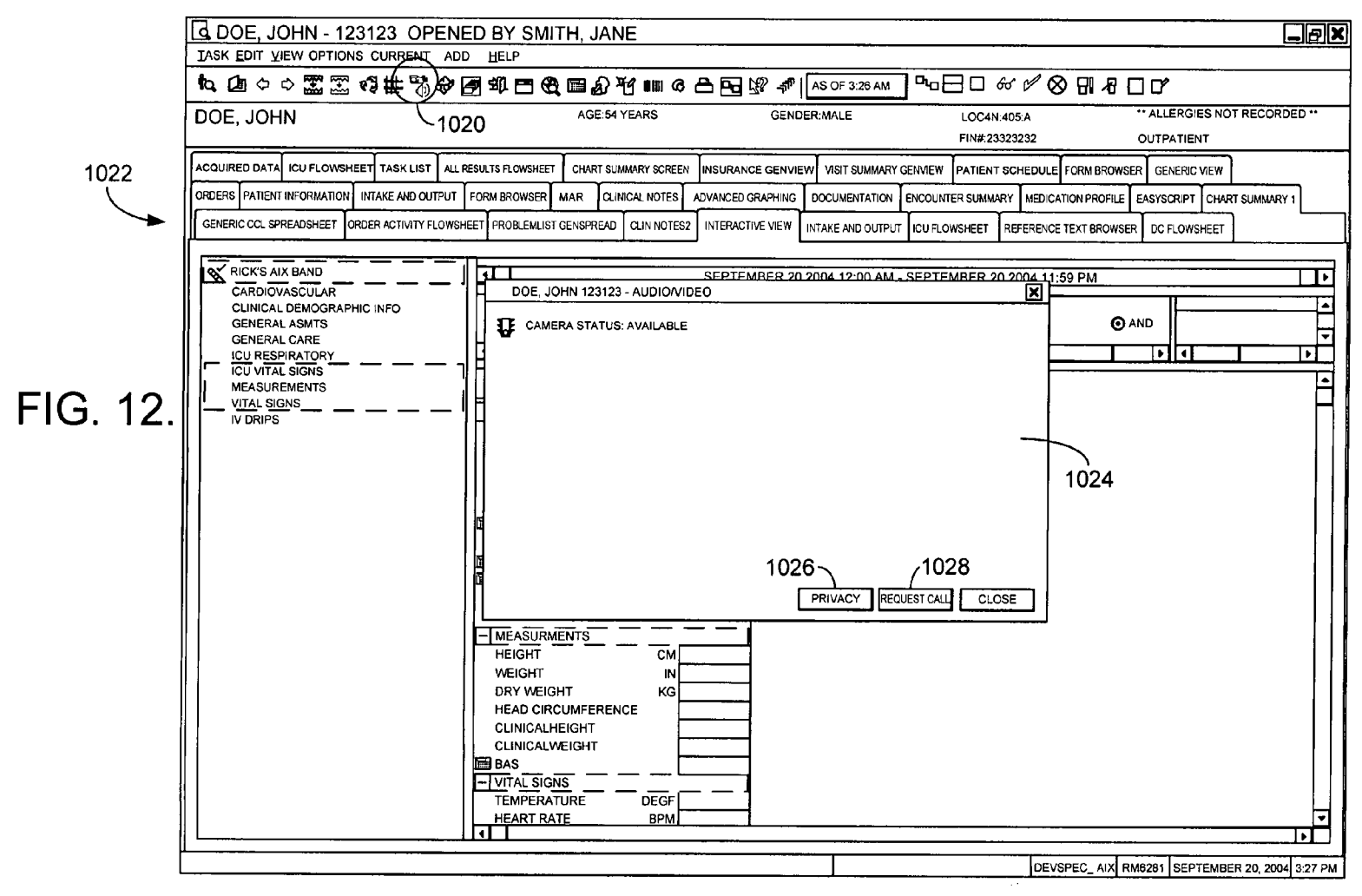

Referring to FIG. 12, an exemplary screen display having a status display 1024 accessible upon selection of the communication initiation option of FIG. 11 by a user at or near the bedside care location is shown and designated generally as reference numeral 1022. The status display 1024 of FIG. 12 indicates that cameras are available for the bedside care location of Mr. Doe. The status display 1024 further includes a "Privacy" indicator 1026, selection of which permits the user to input information regarding the desired communication privacy setting (as more fully described below), and a "Request Call" indicator 1028, selection of which permits the user to request initiation of a communication with a user at a remote care location, as more fully described below.

Figure 13:
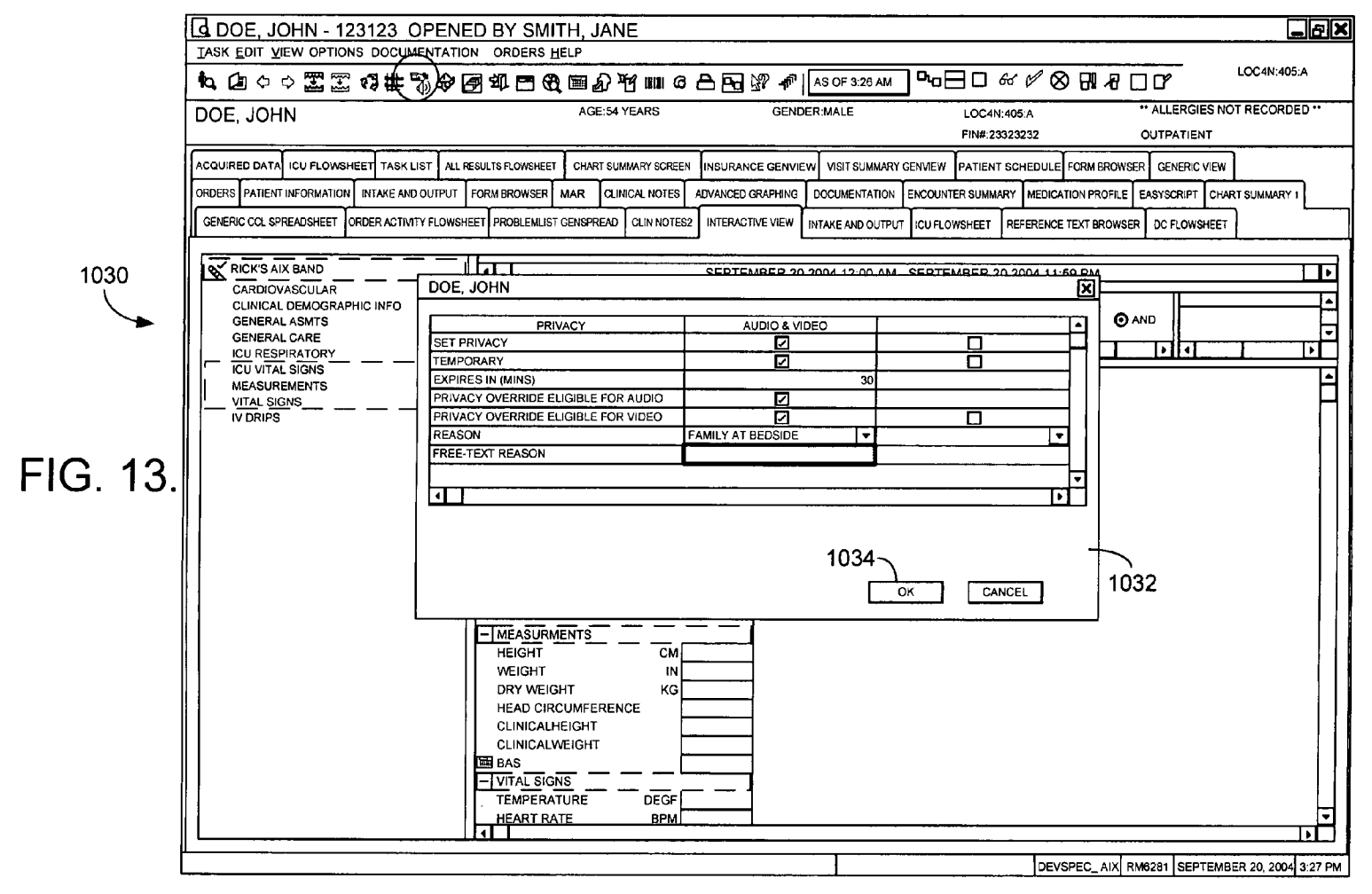

Upon selection of the "Privacy" indicator 1026 of the status display 1024 of FIG. 12, the user at the bedside care location is permitted to input information regarding the desired communication privacy setting. With reference to FIG. 13, an exemplary screen display showing a communication privacy preference display 1032 accessible by selection of the "Privacy" indicator 1026 of FIG. 12 is shown and designated generally as reference numeral 1030. The communication privacy preference display 1032 permits the user to establish a video only communication privacy setting or a combined audio/video communication privacy setting. Though not illustrated, it will be understood by those of ordinary skill in the art that an audio only communication privacy setting may be established as well, if desired.

The communication privacy preference display 1032 further permits the user to indicate if the desired communication privacy setting is temporary and, if so, set a duration for the privacy. The communication privacy preference display 1032 also permits the user at the bedside care location to indicate whether the communication privacy setting is capable of being overridden for each of audio and video communications, as more fully described below. The user may further select a reason for the privacy setting from a preset menu of reasons, or type in a free-text reason as desired.

It will be understood and appreciated by those of ordinary skill in the art that the communication privacy preference display 1032 illustrated in FIG. 13 is exemplary only and is not intended to limit the scope of the present invention in any way. Any display permitting entry of information pertaining to communication privacy settings may be utilized and is contemplated to be within the scope hereof.

Figure 14:
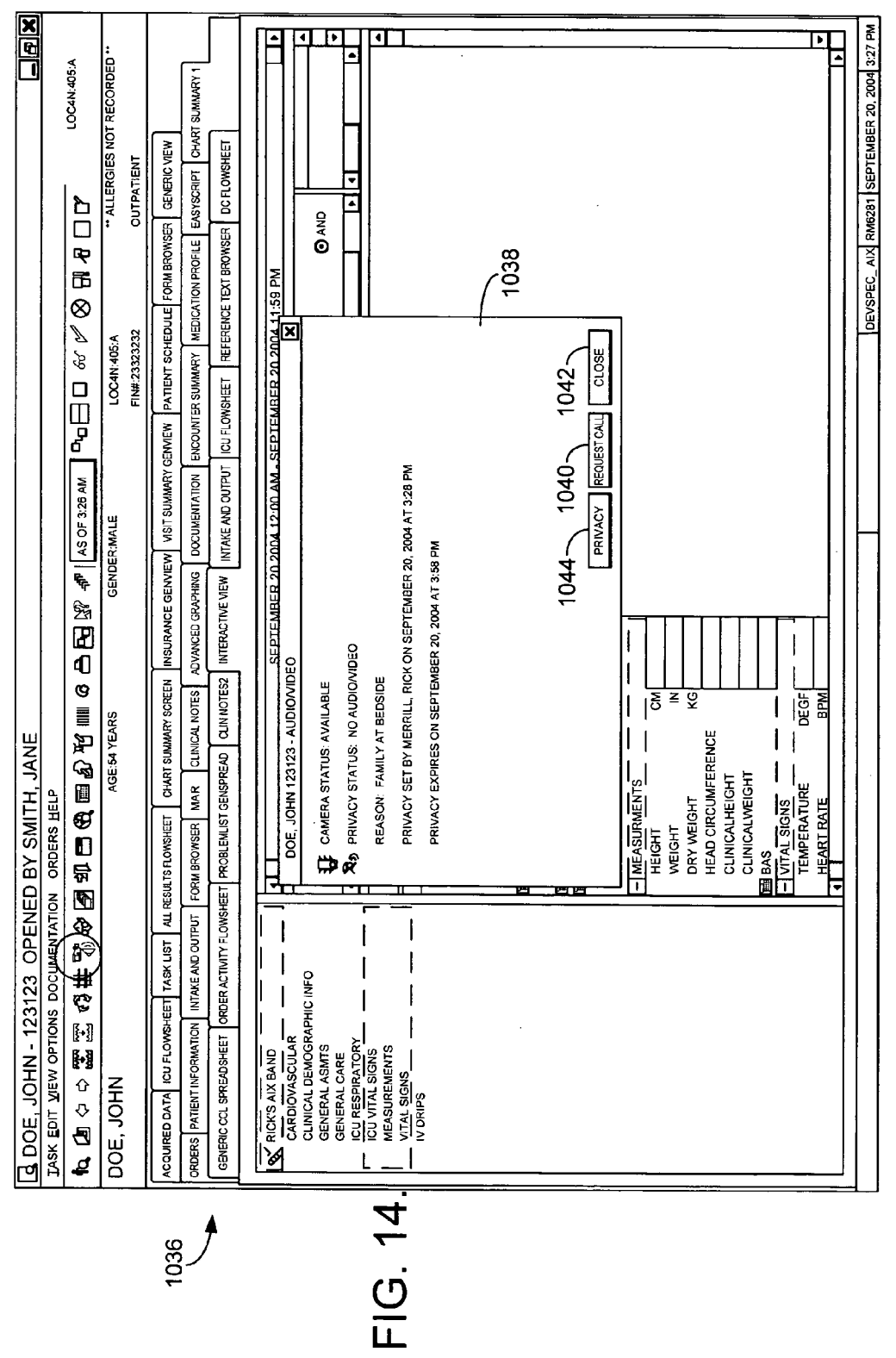

Once the user has input all information regarding the desired communication privacy setting, he or she may select the "OK" indicator 1034. Subsequently, the user may be presented with a screen display 1036 as shown in FIG. 14 wherein an updated status display 1038 indicating that privacy settings have been established and at least a portion of the information input with regard thereto is illustrated.

With reference back to FIG. 9, the system subsequently determines whether a request for initiation of a communication is to be forwarded to the remote care location, as indicated at block 918. In the event that the user at the bedside care location simply desired to establish, modify, or remove a communication privacy setting, he or she may not wish to request a communication with the user at the remote care location. In this scenario, the method is complete, as indicated at block 920. However, if the user at the bedside care location did not desire to establish, modify, or remove a communication privacy setting (or subsequent to the establishment, modification, or removal thereof), he or she may wish to initiate a communication with the user at the remote care location.

Referring back to FIG. 14, if the user in the illustrated exemplary scenario did not wish to initiate a communication with a user at a remote care location, he or she may select the "Close" indicator 1042 to indicate completion of the desired action. If the user desired to modify or remove any of the privacy settings established, he or she may select the "Privacy" indicator 1044 to be returned to the exemplary screen display of FIG. 13.

As previously mentioned, in a currently preferred embodiment, the options available to a user at a bedside care location differ from those available to a user at a remote care location. In this embodiment, a user at a bedside care location may request initiation of a communication with a user at a remote care location but only a user at a remote care location may actually initiate such communication. Thus, upon receipt of a request from a user at a bedside care location for initiation of a communication, the system forwards such request to the remote care location. This is indicated at block 922 of FIG. 9. Once the request has been forwarded, the user at the bedside care location awaits initiation of the communication from the user at the remote care location.

Figure 15:
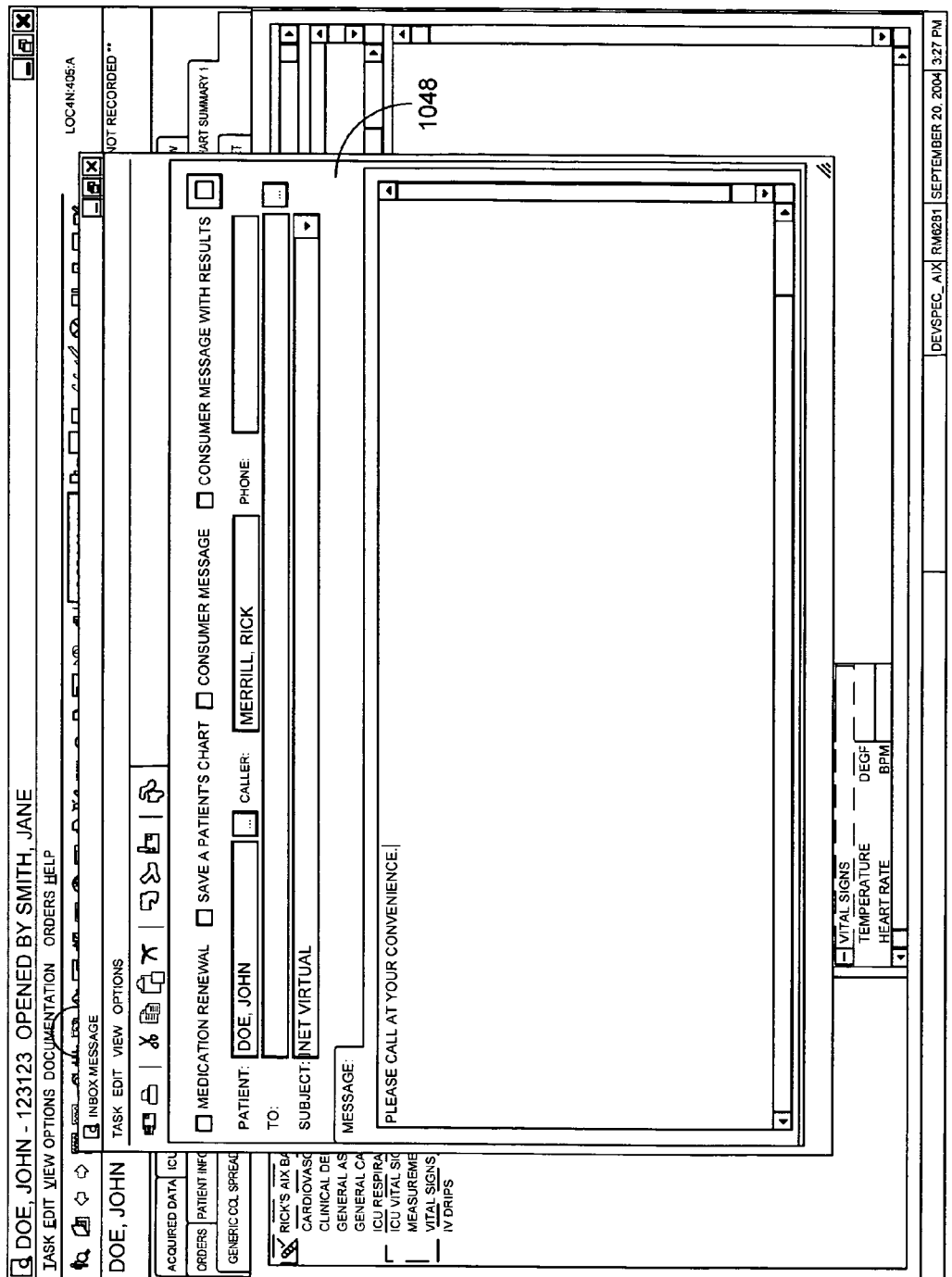
FIG. 15 is an illustrative screen display showing a message display accessible upon selection of the "Request Call" indicator of FIG. 14 in accordance with an embodiment of the present invention.

Referring back to the exemplary screen display 1036 of FIG. 14, if the user at the bedside care location desires to initiate a communication with a user at the remote care location, he or she may select the "Request Call" indicator 1040 whereupon an exemplary screen display 1046 as shown in FIG. 15 may be accessed. The screen display 1046 of FIG. 15 includes a message display 1048 where the user at the bedside care location may input a message requesting initiation of a communication and, if desired, indicate the urgency thereof. Once the user has completed the message, the message may be forwarded to the user at the remote care location who may then initiate a communication with the user at the bedside care location, as more fully described below.

If the bedside user requests initiation of an audio and/or video communication, the system may also post an alert or indicator on a multi-patient display visible by the user at the remote care location to indicate that a session request has been logged for the particular patient, if desired.

Figure 16:
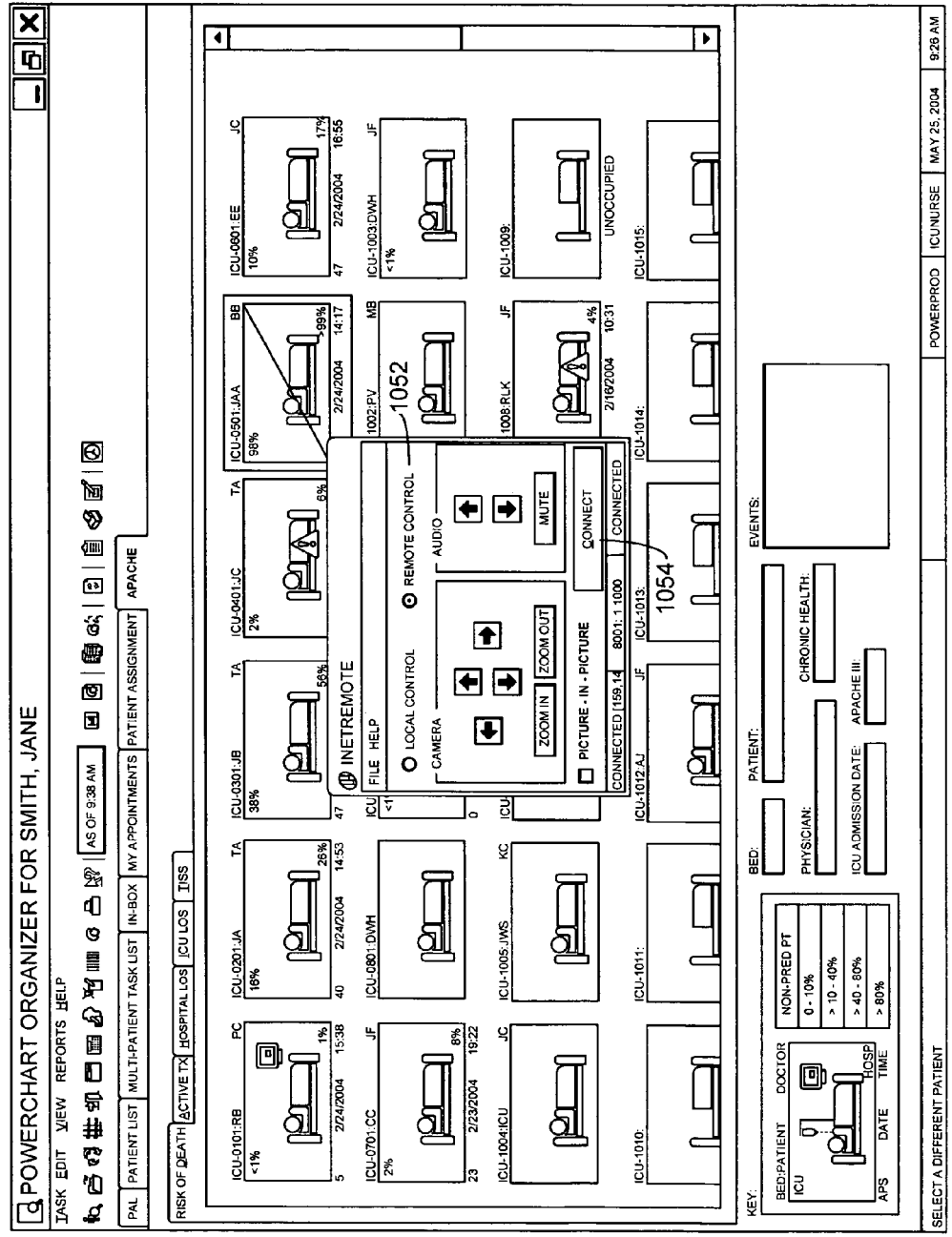
FIG. 16 is an illustrative screen display showing a remote connection display accessible upon selection of the communication initiation option of FIG. 10 by a user at or near the remote care location in accordance with an embodiment of the present invention.

With reference back to FIG. 9, if it determined at block 912 that the user is located at a remote care location rather than a bedside care location, the system next determines whether a communication privacy setting has been established. This is shown at block 924. Referring to FIG. 16, an exemplary screen display 1050 having a remote connection display 1052 accessible upon selection of the communication initiation option 1016 of FIG. 10 by a user at or near the remote care location is illustrated. The remote connection display 1052 includes a "Connect" indicator 1054, selection of which permits the user to initiate (or attempt to initiate, as more fully described below) a communication between the remote care location and the bedside care location.

Referring back to FIG. 9, if it is determined that a communication privacy setting has not been established for the time at which initiation of a communication is desired, the system next establishes the requested audio, video, or combined audio/video communication, as indicated at block 926.

High resolution specifications for the video connection and quality audio connectivity are currently preferred. That is, it is currently preferred that the audio/video connectivity includes reliable, high quality sound and video images and real time communication with at least minimal connection delay, signal breakup, or unexpected signal disconnect. The infrastructure component requirements and configuration necessary to support this implementation are known to those of ordinary skill in the art and, accordingly, are not discussed further herein. Additionally, it is currently preferred that the audio/video transmission shall not create interference with, nor be interfered with by, architectural, mechanical, or biomedical devices that may be present at the bedside and/or remote care locations.

In one embodiment, the audio/video system of the present invention includes the capacity to be "hands free" for both the user at the bedside care location and the user at the remote care location. Additionally, if desired, the audio connectivity provides the capacity to create conference connections between the parties to the communication.

Upon initiation of a communication by a user at the remote care location, the system may output a signal audible in the proximity of the bedside care location indicating that a communication has been established, as indicated at block 928. Further, if desired, the audio/video system of the present invention may output a continuous visual indicator at the bedside care location indicating that the system is transmitting an audio and/or video signal. Still further, the system may display a patient demographic bar on the video display which displays patient demographic information when an audio and/or video communication channel is opened, if desired.

Subsequently, as indicated at block 930, the system may display a plurality of patient views at the remote care location, as more fully described below with reference to FIG. 18. In a currently preferred embodiment, the system of the present invention automatically creates an auditable record for a patient whenever an audio, video, or audio/video communication is established.

With continued reference to FIG. 9, if it is determined at block 924 that a communication privacy setting has been established, the system outputs information regarding the communication privacy setting to the user at the remote care location. This is shown at block 932. Subsequently, as indicated at block 934, the system determines whether or not the established communication privacy setting is capable of being overridden by the user at the remote care location. If the communication privacy setting is not capable of being overridden, the method is complete and establishment of a communication between a user at the bedside care location and a user at the remote care location is not permitted. This is shown at block 936.

If, however, it is determined that the established communication privacy setting is capable of being overridden, the system next determines whether or not the user at the remote care location wishes to override the setting. This is shown at block 938. If the user at the remote care location does not indicate a desire to override the communication privacy setting, the method is complete, as indicated at block 936, and a communication between the user at the remote care location and the user at the bedside care location is not established. If, however, it is determined that the user at the remote care location does wish to override the communication privacy setting, the system next establishes the requested communication, as shown at block 926. The method steps indicated at block 926 through 930 subsequently proceed as described hereinabove.

Figure 17:
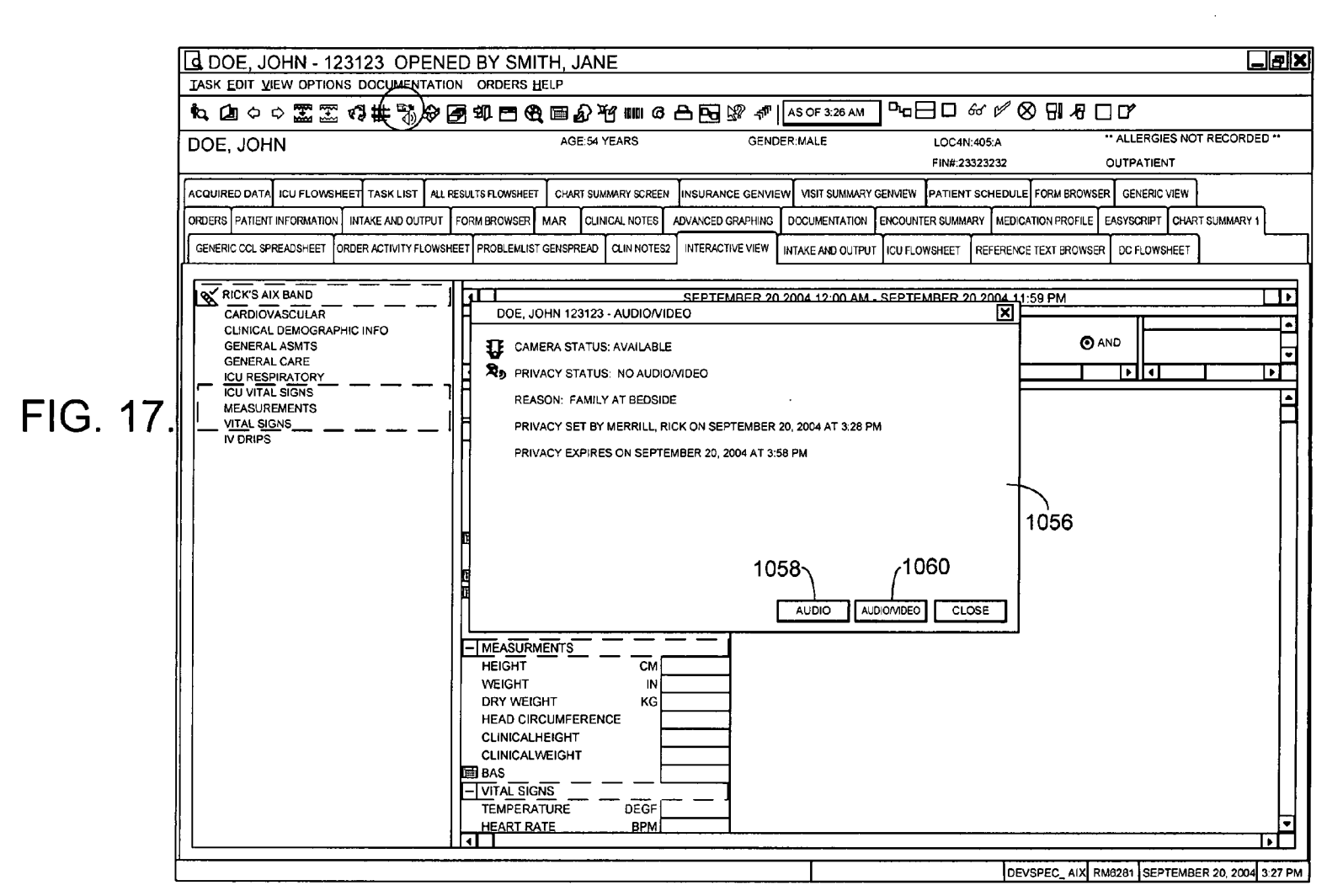

With reference to FIG. 17, an exemplary screen display showing a communication privacy setting status display accessible upon selection of the "Connect" indicator 1054 of FIG. 16 in the event it is determined that a communication privacy setting has been established is shown and designated generally as reference numeral 1056. The communication privacy setting status display 1056 indicates that video connectivity is available for Mr. Doe's bedside care location but that a temporary privacy setting has been established as the patient's family is at the bedside. In this scenario, the system has determined that the communication privacy setting is capable of being overridden and, accordingly, an "Audio" indicator 1058 and an "Audio/Video" indicator 1060 are illustrated, selection of which will initiate the indicated communication. Although not illustrated, it will be understood by those of ordinary skill in the art that a "Video" only indicator may also be present in the communication privacy setting status display 1056, if desired.

With reference back to FIG. 9, upon establishment of a communication between a user at the bedside care location and a user at the remote care location, the system displays a plurality of patient views to the user at the remote care location. This is indicated at block 930. With reference to FIG. 18, a schematic diagram showing a plurality of different patient views simultaneously displayed to a user at a remote care location is illustrated. It will be understood and appreciated by those of ordinary skill in the art that the plurality of different patient views may be displayed on a plurality of different display devices as shown, or may be displayed on different portions of a single display. All such variations are contemplated to be within the scope hereof.

Figure 18:
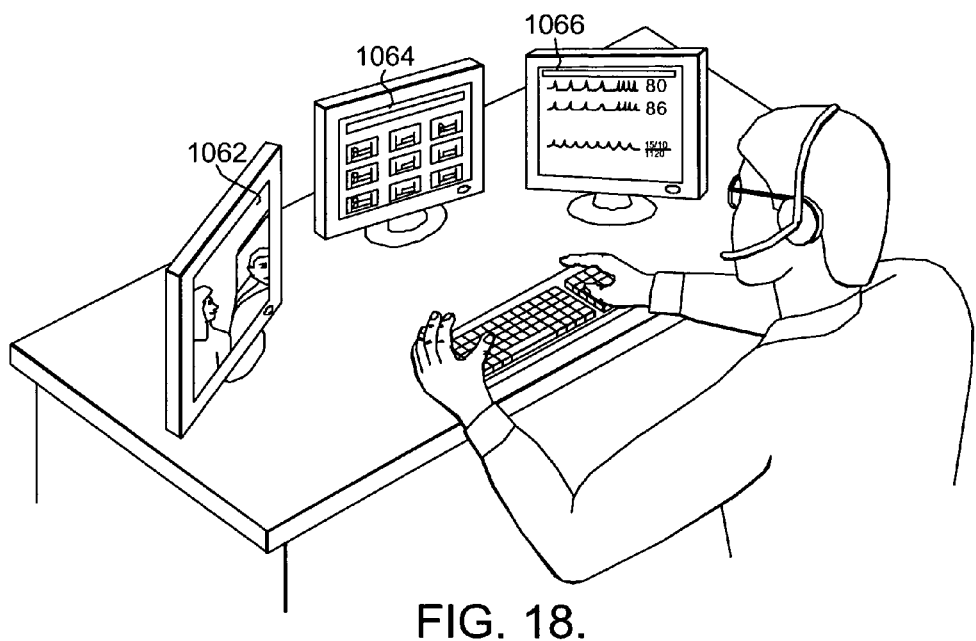
FIG. 18 is a schematic diagram showing a plurality of different patient views simultaneously displayed to a user at the remote care location, one such view being a video or audio/video connection display, in accordance with an embodiment of the present invention.

In the schematic diagram of FIG. 18, the patient views displayed include a video or audio/video connection display 1062, a multi-patient view display 1064, and a monitored data view display 1066. It will be understood by those of ordinary skill in the art, however, that the illustrated views are merely exemplary in nature and not intended to limit the scope of the present invention in any way. Any information pertaining to the patient occupying the bedside care location in question, including reference materials and the like, may be displayed and all such variations are contemplated to be within the scope hereof. For example, in addition to the displays 1062, 1064 and 1066, a fourth display of the electronic medical record for the selected patient may be employed.

In one embodiment of the present invention, the system may permit the user at the remote care location to launch an audio and/or video communication channel with an unoccupied bedside care location. However, the system may display a warning demographic-type banner on the video display alerting the user at the remote care location that no patient is assigned to the bedside care location in question. The system may recognize when a patient is later assigned to the bedside care location and may update the demographic header on the video display accordingly. This embodiment accommodates those circumstances when a patient is directly admitted to an empty patient care location without having been registered in the system. An example would be an emergent admission where the admitting department has not yet had an opportunity to register the patient into the system or information input into the admitting department's external patient entry system has not crossed into the system supporting the multi-patient view.

Additional embodiments of present invention may permit one way viewing of a video connection at the remote care location or may permit two-way viewing of the video connection for the users at the remote and bedside care locations. Additionally, the system may permit the user at the remote and/or bedside care locations to zoom in or out to enhance their view of the patient (or remote user, if desired) with the camera visual field being dependent on the positioning of the camera.

In a currently preferred embodiment, the system of the present invention supports having multiple patient charts open at a single point in time. However, if the user at the remote care location initiates an audio and/or video connection from any location other than the patient chart, and has multiple patient charts open, the system may automatically bring the patient record for the patient with whom the audio and/or video communication has been established to the front if that chart is already open on the user's desktop. If, however, the user, at the remote care location initiates an audio and/or video communication from any location other than the patient chart and the chart for the patient for whom the audio and/or video communication has been established is not open, the patient's chart may automatically be opened and be brought to the forefront of the user's display.

In summary, the present invention provides a computerized method and system for outputting at least one patient alert from a multi-patient display. The present invention further provides a computerized method and system for establishing a communication between a bedside care location and a remote care location. If desired, the present invention may permit these abilities twenty-four hours a day, seven days a week.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated and within the scope of the claims.

What is claimed is:

1. One or more tangible computer storage media having computer-executable instructions stored thereon that execute a method in a patient care computing system environment for establishing a communication between a bedside care location and a remote care location, the method comprising:
   providing a multi-patient display having a plurality of selectable patient indicators, each of the selectable patient indicators corresponding with a patient care location;
   receiving an indication that one of the plurality of selectable patient indicators has been selected by a user, wherein the user's selection is indicative of a request for initiation of an audio communication and a video communication between the user located at the remote care location and another party located at the bedside care location, the video communication utilizing one or more cameras;
   determining that a communication privacy setting is to be established; and
   receiving input regarding one or more of a nature of the communication privacy setting to be established, a duration of the communication privacy setting to be established, and an indication of whether the communication privacy setting is capable of being overridden.

2. The media of claim 1, further comprising forwarding the request for initiation of the communication to the bedside care location.

3. The media of claim 1, the method further comprises receiving input regarding a reason for the communication privacy setting.

4. The media of claim 1, wherein the nature of the communication privacy setting to be established comprises one of a temporary communication privacy setting and a permanent communication privacy setting.

5. The media of claim 1, further comprising communicating the request for initiation of the audio communication and the video communication.

6. The media of claim 5, further comprising determining whether the communication privacy setting has been established.

7. The media of claim 6, wherein if it is determined that the communication privacy setting has not been established, the method further comprises establishing the requested communication between the remote care location and the bedside care location.

8. The media of claim 7, further comprising outputting a signal audible at the bedside care location once a communication has been established.

9. The media of claim 7, wherein upon establishing the requested communication between the remote care location and the bedside care location, the method further comprises displaying a plurality of different patient views at the remote care location.

10. The media of claim 9, wherein each of the plurality of different patient views is capable of being a view of an electronic record associated with a patient, real-time monitored patient data, the multi-patient display, and a video display of the bedside care location.

11. The media of claim 7, wherein upon establishing the requested communication between the remote care location and the bedside care location, the method further comprises automatically displaying an electronic record associated with a patient corresponding to the one of the selectable patient indicators.

12. The media of claim 6, wherein if it is determined that the communication privacy setting has been established, the method further comprises outputting at least one of a nature of the communication privacy setting established, a duration of the communication privacy setting that has been established, a reason for the communication privacy setting, and an indication whether the communication privacy setting is capable of being overridden.

13. The media of claim 12, wherein if it is determined that the communication privacy setting is capable of being overridden, the method further comprises determining whether or not the communication privacy setting is to be overridden.

14. The media of claim 13, wherein if it is determined that the communication privacy setting is to be overridden, the method further comprises establishing the requested communication between the remote care location and the bedside care location.

15. The media of claim 14, further comprising outputting a signal audible at the bedside care location once a communication has been established.

16. The media of claim 14, wherein upon establishing the requested communication between the remote care location and the bedside care location, the method further comprises displaying a plurality of different patient views at the remote care location.

17. The media of claim 16, wherein each of the plurality of different patient views is capable of being a view of an electronic record associated with a patient, real-time monitored patient data, the multi-patient display, and a video display of the bedside care location.

18. A method in a patient care computing system environment using a computing device for establishing a communication between a bedside care location and a remote care location, the method comprising:
   displaying an electronic medical record associated with a patient, the electronic medical record having a selectable audio and video initiation indicator;
   receiving an indication that the selectable audio and video initiation indicator has been selected by a user, wherein the user's selection is indicative of a request for initiation of an audio communication and a video communication between the user and another party, the video communication utilizing one or more cameras;
   determining that a communication privacy setting is to be established; and
   receiving input regarding one or more of a nature of the communication privacy setting to be established, a duration for which the communication privacy setting is to be established, a reason for the communication privacy, and an indication whether the communication privacy setting may be overridden.

19. The method of claim 18, wherein the user is located at the bedside care location and the other party is located at the remote care location.

20. The method of claim 19, further comprising forwarding the request for initiation of the communication to the remote care location.

21. The method of claim 18, wherein the nature of the communication privacy setting to be established comprises one of a temporary communication privacy setting and a permanent communication privacy setting.

22. The method of claim 18, wherein the user is located at the remote care location and the other party is located at the bedside care location.

23. The method of claim 22, further comprising determining whether a communication privacy setting has been established.

24. The method of claim 23, wherein if it is determined that the communication privacy setting has not been established, the method further comprises establishing the requested communication between the remote care location and the bedside care location.

25. The method of claim 24, further comprising outputting a signal audible at the bedside care location once a communication has been established.

26. The method of claim 24, wherein upon establishing the requested communication between the remote care location and the bedside care location, the method further comprises displaying a plurality of different patient views at the remote care location.

27. The method of claim 26, wherein each of the plurality of different patient views is capable of being a view of an electronic record associated with a patient, real-time monitored patient data, the multi-patient display, and a video display of the bedside care location.

28. The method of claim 23, wherein if it is determined that a communication privacy setting has been established, the method further comprises displaying at least one of a nature of the communication privacy setting established, a duration for which the communication privacy setting has been established, a reason for the communication privacy setting, and an indication whether the communication privacy setting is capable of being overridden.

29. The method of claim 28, wherein if it is determined that the communication privacy setting is capable of being overridden, the method further comprises receiving input indicative of whether or not the communication privacy setting is to be overridden.

30. The method of claim 29, wherein if it is determined that the communication privacy setting is to be overridden, the method further comprises establishing the requested communication between the remote care location and the bedside care location.

31. The method of claim 30, further comprising outputting a signal audible at the bedside care location that a communication has been established.

32. The method of claim 30, wherein upon establishing the requested communication between the remote care location and the bedside care location, the method further comprises displaying a plurality of different patient views at the remote care location.

33. The method of claim 32, wherein each of the plurality of different patient views is capable of being a view of an electronic record associated with a patient, real-time monitored patient data, the multi-patient display, and a video display of the bedside care location.

\* \* \* \* \*